United States Patent
Schings

(10) Patent No.: US 11,399,827 B2
(45) Date of Patent: Aug. 2, 2022

(54) SEPARATION MECHANISM FOR SURGICAL LINEAR CUTTER

(71) Applicant: Ethicon LLC, Guaynabo, PR (US)

(72) Inventor: Brian D. Schings, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 34 days.

(21) Appl. No.: 16/886,924

(22) Filed: May 29, 2020

(65) Prior Publication Data

US 2021/0369272 A1    Dec. 2, 2021

(51) Int. Cl.
*A61B 17/072*    (2006.01)
*A61B 17/11*    (2006.01)
*A61B 17/115*    (2006.01)
*A61B 17/00*    (2006.01)

(52) U.S. Cl.
CPC .......... *A61B 17/072* (2013.01); *A61B 17/115* (2013.01); *A61B 17/1114* (2013.01); *A61B 2017/00367* (2013.01); *A61B 2017/00477* (2013.01); *A61B 2017/00876* (2013.01); *A61B 2017/07264* (2013.01); *A61B 2017/07271* (2013.01); *A61B 2017/07285* (2013.01)

(58) Field of Classification Search
CPC .............. A61B 17/072; A61B 17/1114; A61B 17/115; A61B 17/105; A61B 2017/0047; A61B 2017/07214; A61B 2017/07271; A61B 2017/2927; A61B 2017/2946; A61B 2017/07285; A61B 2017/00473
See application file for complete search history.

(56) References Cited

U.S. PATENT DOCUMENTS

| | | | | |
|---|---|---|---|---|
| 4,608,981 A | * | 9/1986 | Rothfuss | A61B 17/07207 227/180.1 |
| 5,718,359 A | * | 2/1998 | Palmer | A61B 17/07207 227/175.2 |
| 5,878,938 A | * | 3/1999 | Bittner | A61B 17/07207 227/175.4 |
| 7,334,717 B2 | * | 2/2008 | Rethy | A61B 17/105 227/175.1 |
| 9,402,629 B2 | * | 8/2016 | Ehrenfels | A61B 17/105 |

(Continued)

OTHER PUBLICATIONS

U.S. Appl. No. 16/886,919, entitled "Surgical Linear Cutter Wishbone Separation Mechanism with Detent," filed May 29, 2020.

(Continued)

*Primary Examiner* — Nathaniel C Chukwurah
(74) *Attorney, Agent, or Firm* — Frost Brown Todd LLC

(57) ABSTRACT

An apparatus includes a first portion having a handle and a jaw, a second portion having a handle and a jaw, a latching member, and a proximal coupling assembly. The second portion may selectively pivot about a proximal location relative to the first portion. The latching member drives the first jaw and the second jaw toward a fully closed configuration. The first jaw and second jaw may clamp, cut, and staple tissue between the jaws. The proximal coupling selectively attaches the first portion with the second portion. The proximal coupling includes a pivot body and a coupling body. The pivot body is pivotally attached to the first portion at the proximal location. The coupling body, which is associated with the second portion, engages the pivot body at a location distal to the proximal location to selectively attach the first portion with the second portion.

20 Claims, 31 Drawing Sheets

(56) References Cited

U.S. PATENT DOCUMENTS

| | | | |
|---|---|---|---|
| 2010/0072253 A1* | 3/2010 | Baxter, III | A61B 17/07207 227/176.1 |
| 2019/0239883 A1 | 8/2019 | Baxter, III et al. | |
| 2020/0046350 A1 | 2/2020 | Deck et al. | |
| 2020/0046351 A1 | 2/2020 | Jones et al. | |
| 2020/0046353 A1 | 2/2020 | Deck et al. | |

OTHER PUBLICATIONS

U.S. Appl. No. 16/886,920, entitled "Pin Trap Mechanism for Surgical Linear Cutter," filed May 29, 2020.
International Search Report and Written Opinion dated Oct. 13, 2021 for Application No. PCT/EP2021/064375, 10 pgs.

* cited by examiner

SEPARATION MECHANISM FOR SURGICAL LINEAR CUTTER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened, and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
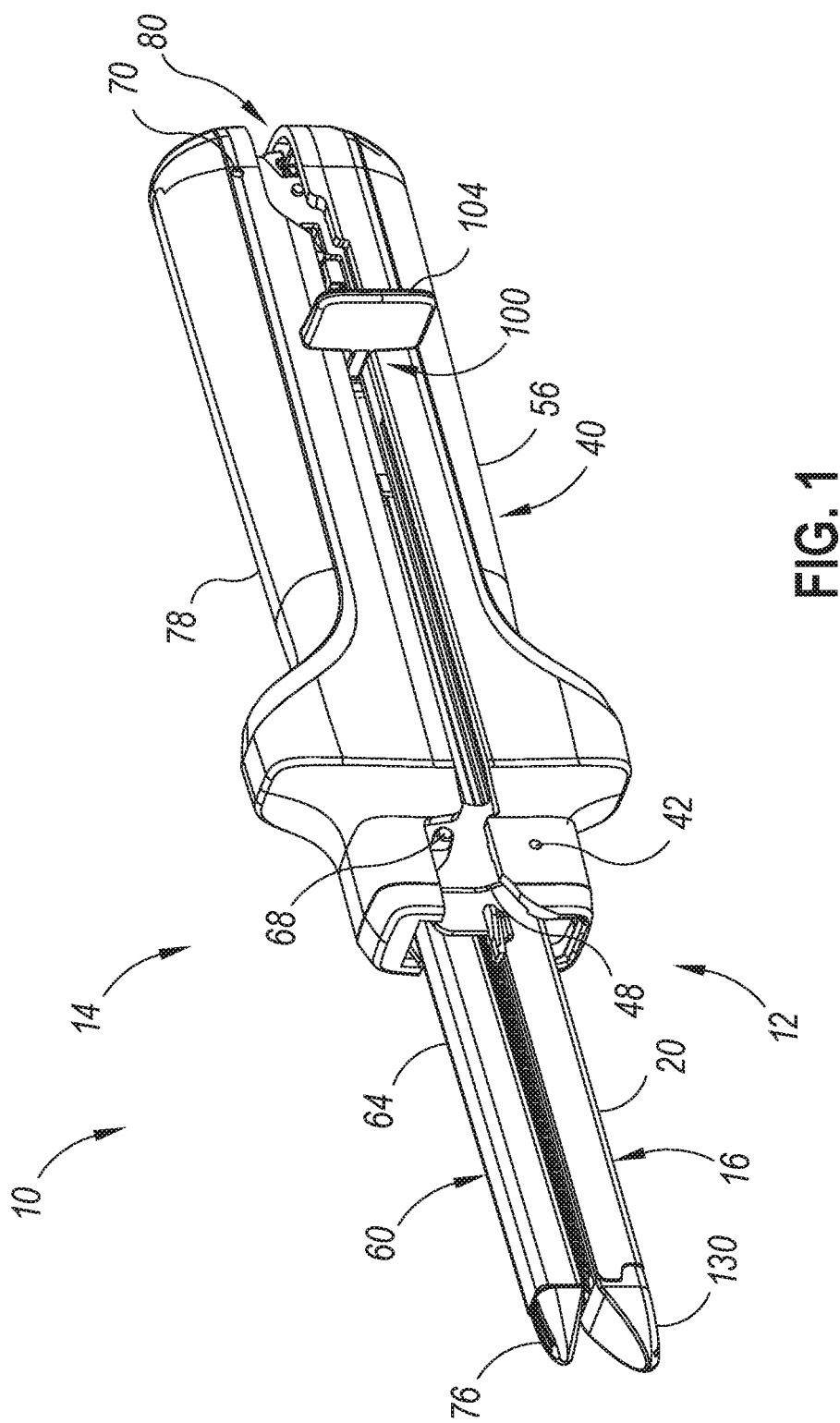
FIG. 1 depicts a perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
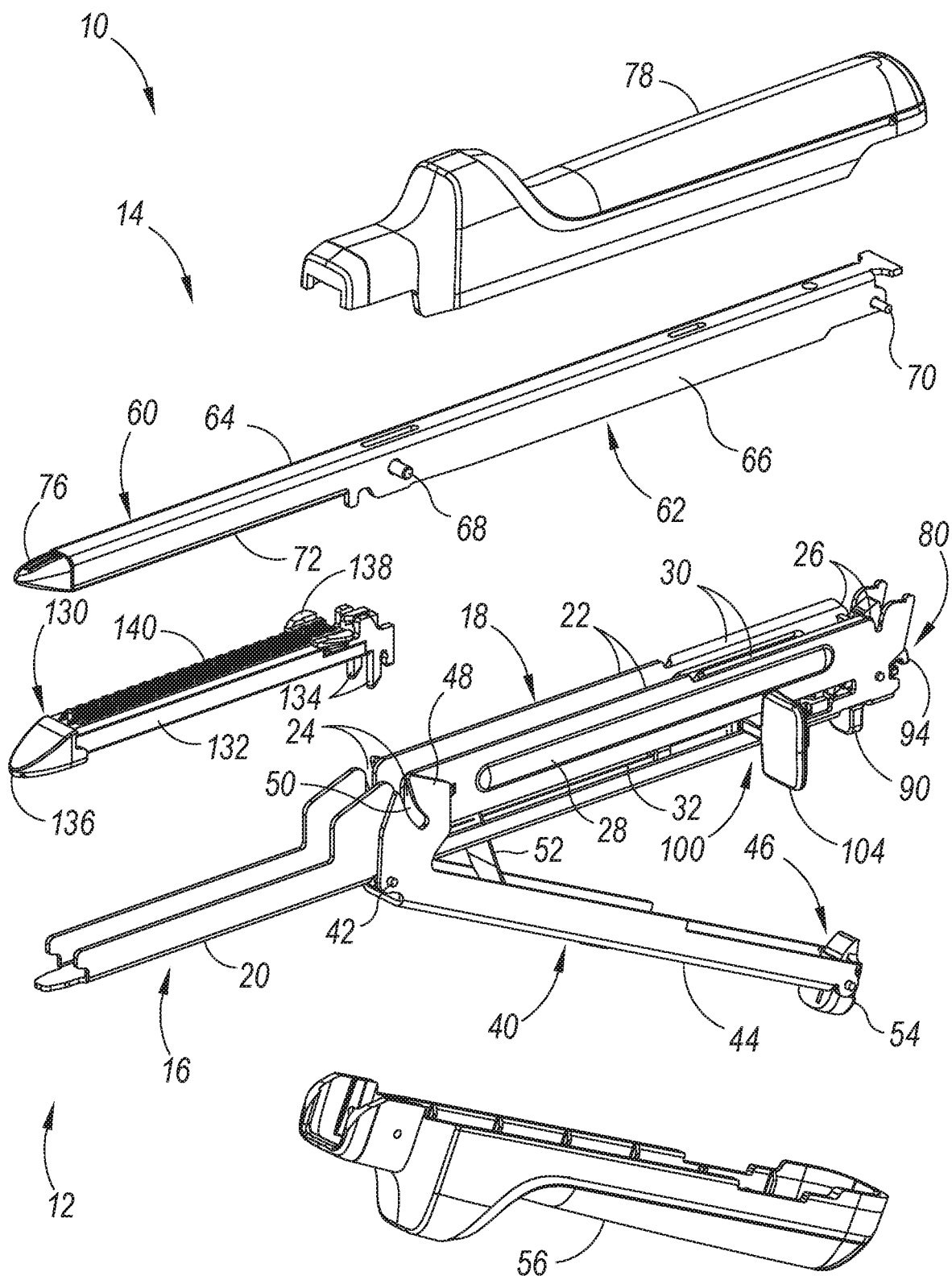
FIG. 2 depicts an exploded perspective view of the linear surgical stapler of FIG. 1.

FIGS. 1-2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween for simultaneous cutting and stapling of the clamped tissue.

Cartridge half (12) includes an elongate cartridge channel (16) having a proximal frame portion (18) and a distal jaw portion (20). Proximal frame portion (18) slidably retains a firing assembly (100) and includes a laterally opposed pair of upright side flanges (22). Each side flange (22) includes a vertical slot (24) arranged at a distal end thereof, and a tapered notch (26) arranged at a proximal end thereof. An outwardly projecting stiffening rib (28) extends longitudinally between the distal slot (24) and proximal notch (26) of each side flange (22) and is configured to provide the side flange (22) with enhanced stiffness. An outwardly flared upper segment (30) defines an upper edge of a proximal portion of each side flange (22) and is configured to facilitate receipt of anvil half (14) by cartridge half (12). Each side flange (22) further includes an elongate firing slot (32) extending longitudinally between proximal notch (26) and distal slot (24) along a lower side of side flange (22). Elongate firing slots (32) are configured to guide firing assembly (100) between proximal and distal positions. Firing assembly (100) is described in greater detail below in connection with FIG. 4. Distal jaw portion (20) of cartridge channel (16) is configured to receive a staple cartridge (130) (or "reload").

Cartridge half (12) further includes a clamp lever (40) (also referred to as a "latch lever") pivotably coupled to cartridge channel (16) with a clamp lever pivot pin (42), which is arranged in approximate alignment with distal slots (24) of cartridge channel side flanges (22). Clamp lever (40) includes an elongate lever arm (44) having a free proximal end (46) and a distal end that is pivotably coupled to a lower portion of cartridge channel (16) with pivot pin (42). A pair of opposed jaws (48) extend distally from the distal end of lever arm (44) alongside cartridge channel side flanges (22). Each jaw (48) includes a curved slot (50) having a closed proximal end and an open distal end configured to receive a latch pin (68) of anvil half (14), as described below.

Figure 3:
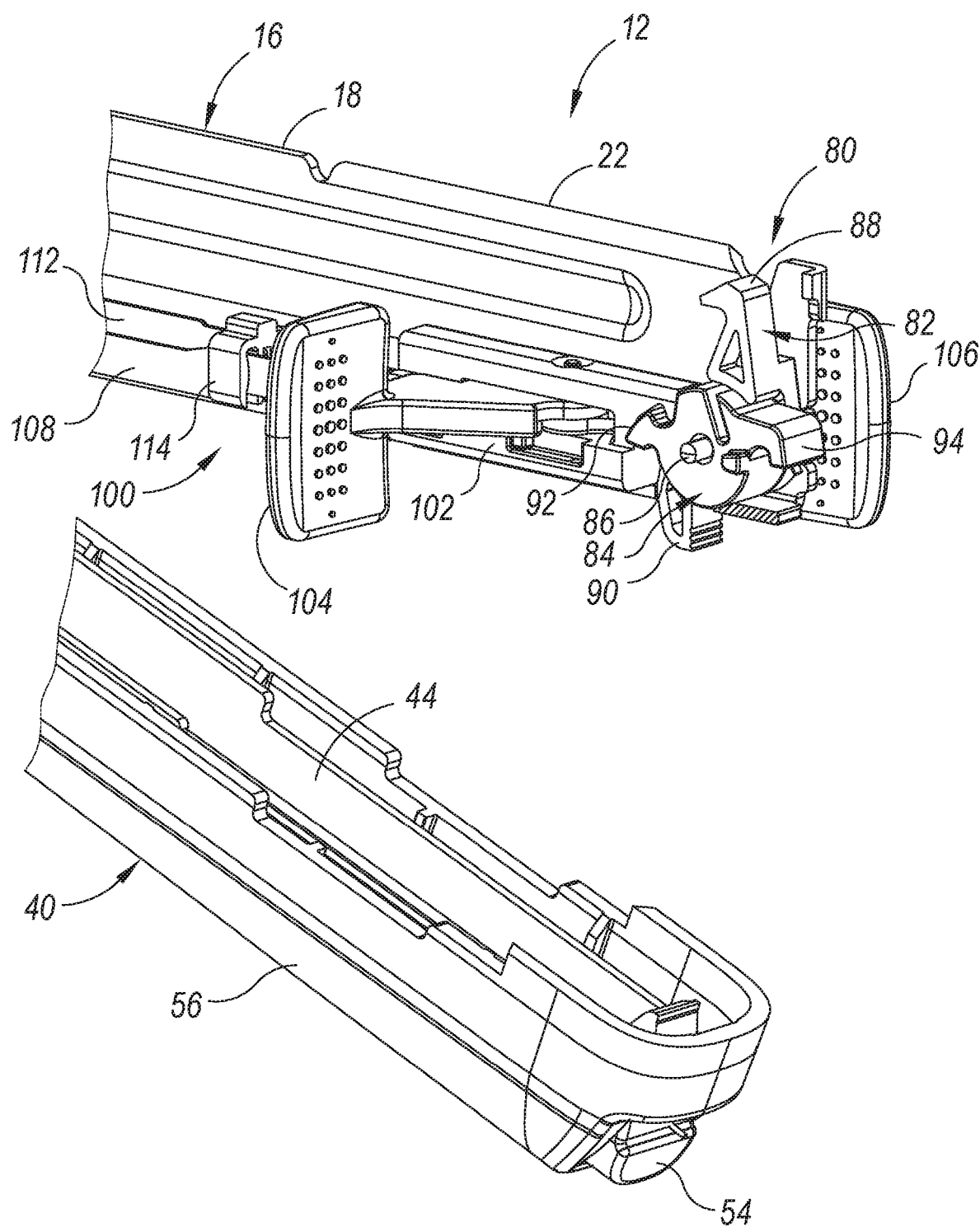
FIG. 3 depicts a perspective view of a proximal portion of the cartridge half of the linear surgical stapler of FIG. 1, showing a cartridge channel in cross-section and the clamp lever in an open position to reveal internal features of the cartridge half.

Clamp lever (40) is operable to pivot relative to cartridge channel (16) between an open position in which proximal end (46) of lever arm (44) is spaced from cartridge channel frame portion (18), and a closed position in which proximal end (46) confronts cartridge channel frame portion (18). Actuation of clamp lever (40) from the open position to the closed position operates to capture the opposed lateral ends of latch pin (68) within clamp lever jaw slots (50), and thereby clamp anvil half (14) against cartridge half (12), as shown and described below in connection with FIGS. 5C-5D. In that regard, the curvature of each jaw slot (50) defines respective upper and lower camming surfaces configured to engage and draw the respective lateral end of latch pin (68) toward cartridge channel (16) as clamp lever (40) is pivotably closed. A resilient member shown in the form of a flat spring (52) biases lever arm (44) toward the open position. Accordingly, flat spring (52) promotes disengagement of clamp lever jaws (48) from anvil half latch pin (68) upon initial advancement of clamp lever (40) from the closed position toward the open position. As best shown in FIGS. 2 and 3, clamp lever (40) further includes a latch member (54) arranged at proximal end (46) of lever arm (44). Clamp lever latch member (54) is configured to resiliently and releasably engage a proximal end of cartridge channel frame portion (18) and thereby releasably retain clamp lever (40) in the closed position, for instance while stapler (10) is being fired.

Anvil half (14) of linear surgical stapler (10) includes an elongate anvil channel (60) having a proximal frame portion (62) and a distal jaw portion (64). Proximal frame portion (62) includes a laterally opposed pair of upright side flanges (66) that are configured to be received between cartridge channel side flanges (22) when anvil half (14) is coupled with cartridge half (12). A distal latch projection in the form of latch pin (68) extends laterally through the distal ends of anvil channel side flanges (66), and a proximal pivot projection in the form of a proximal pin (70) extends laterally through the proximal ends of anvil channel side flanges (66). Anvil pins (68, 70) are configured to facilitate coupling of anvil half (14) with cartridge half (12), as described below.

Distal jaw portion (64) of anvil half (14) supports an anvil plate (72) that defines an anvil surface having a plurality of staple forming pockets configured to deform legs of staples ejected by staple cartridge (130) when stapler (10) is fired, for example as described in greater detail below. In some versions, the anvil surface may be formed integrally with distal jaw portion (64). Distal jaw portion (64) of anvil half (14) additionally supports a tapered distal tip member (76). In some versions, distal tip member (76) may be selectively extendable relative to distal jaw portion (64) in accordance with the teachings of U.S. Pat. Pub. No. 2020/0046351, entitled "Decoupling Mechanism for Linear Surgical Stapler," published on Feb. 13, 2020, issued as U.S. Pat. No. 11,033,266 on Jun. 15, 2021, the disclosure of which is incorporated by reference herein.

As shown in FIG. 2, linear surgical stapler (10) further includes a plurality of shrouds (56, 78) that cover select portions of stapler (10) and promote effective grip and manipulation of stapler (10) by an operator during use. In the present example, a clamp lever shroud (56) is affixed to and covers an outwardly facing side of clamp lever (40) such that clamp lever shroud (56) is configured to pivot with clamp lever (40) relative to cartridge channel (16). Additionally, an anvil shroud (78) is affixed to and covers an outwardly facing side of anvil channel (60). In some versions, anvil shroud (78) may be coupled with anvil channel (60) in accordance with the teachings of U.S. Pat. Pub. No. 2020/0046353, entitled "Clamping Assembly for Linear Surgical Stapler," published on Feb. 13, 2020, issued as U.S. Pat. No. 11,278,285 on Mar. 22, 2022, the disclosure of which is incorporated by reference herein. It will be appreciated that in other versions, shrouds (56, 78) may be coupled with clamp lever (40) and anvil channel (60) in a variety of other suitable manners readily apparent to those of ordinary skill in the art.

As shown best in FIG. 3, a proximal end of cartridge half (12) includes a retaining assembly (80) configured to releasably retain portions of anvil half (14) and firing assembly (100). Retaining assembly (80) of the present example includes an anvil latch member (82) and a detent member (84), both of which are rotatably coupled with a proximal end of cartridge channel (16) via a laterally extending pin (86) arranged proximally of firing slots (32). A torsion spring (not shown) is configured to resiliently bias anvil latch member (82) and detent member in opposite rotational directions about the lateral axis defined by pin (86).

Anvil latch member (82) includes an upper finger (88) configured to releasably capture proximal anvil pin (70) when pin (70) is directed into proximal tapered notches (26) of cartridge channel (16), thereby coupling the proximal ends of stapler halves (12, 14). A lower end of anvil latch member (82) defines a release button (90) configured to be depressed by the operator when clamp lever (40) is in the open position to release proximal pin (70) from latch finger (88) and thereby permit separation of the proximal ends of stapler halves (12, 14). Detent member (84) includes a distal finger (88) configured to releasably capture the proximal end of a slide block (102) of firing assembly (100) when firing assembly (100) us in a proximal home position, shown in FIG. 3. Detent member (84) further includes a proximal hook (94) configured to releasably capture an upper tip of clamp lever latch member (54) while slide block (102) is positioned distally of its proximal home position, thereby preventing actuation of clamp lever latch member (54) and opening of clamp lever (40) during firing of stapler (10). When firing assembly (100) is in its proximal home position (i.e., before or after firing of stapler (10)), proximal hook (94) of detent member (84) permits clamp lever latch member (54) to rotatably disengage proximal frame portion (18) of cartridge channel (16) in response to actuation by the operator. As a result, clamp lever (40) may then be opened. Retaining assembly (80) and related components of cartridge half (12) may be further configured and operable in accordance with at least some of the teachings of U.S. Pat. Pub. No. 2020/0046350, entitled "Firing System for Linear Surgical Stapler," published on Feb. 13, 2020, issued as U.S. Pat. No. 10,898,187 on Jan. 26, 2021, the disclosure of which is incorporated by reference herein.

Figure 4:
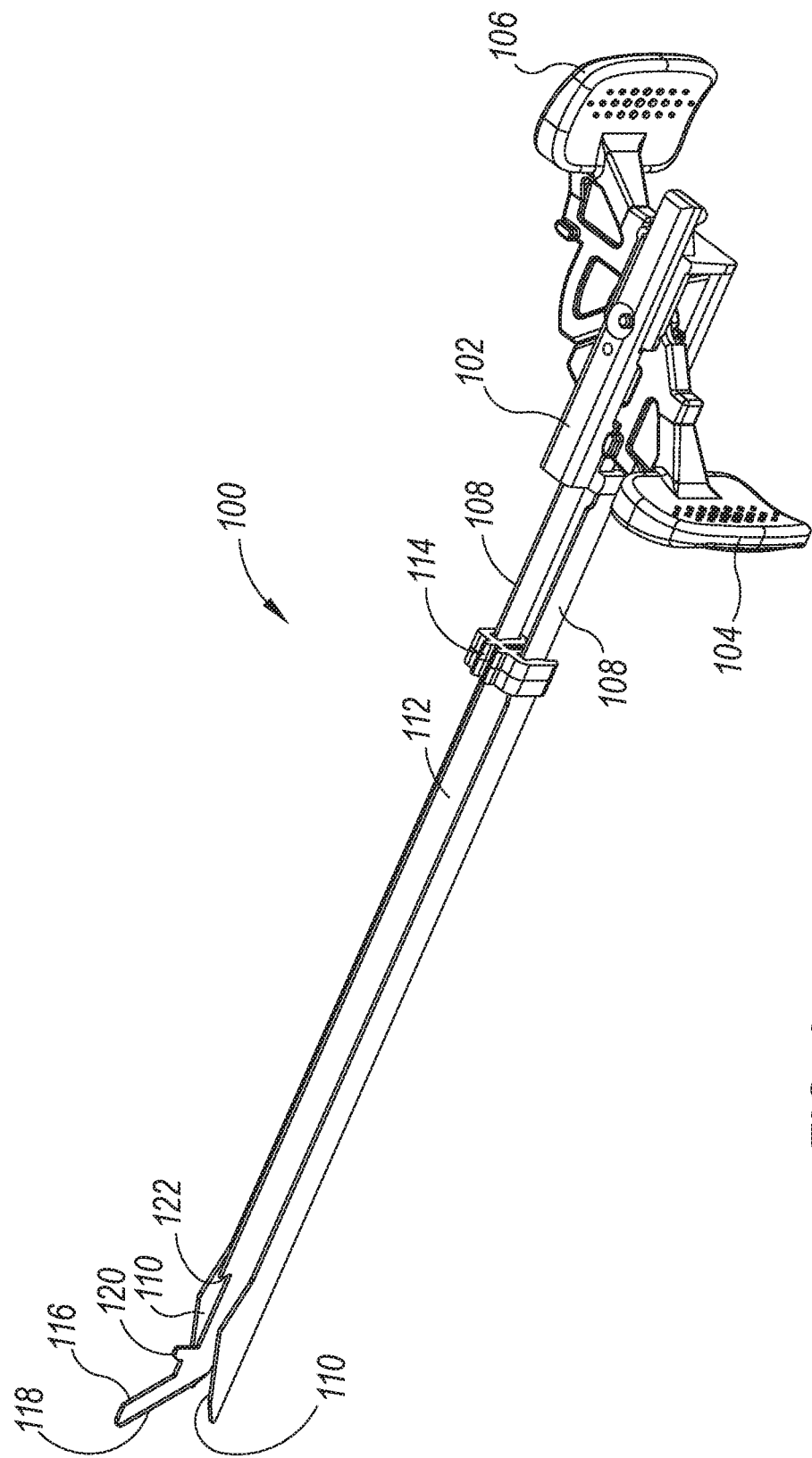
FIG. 4 depicts a top perspective view of a firing assembly of the linear surgical stapler of FIG. 1.

As shown best in FIG. 4, firing assembly (100) of cartridge half (12) includes slide block (102), a pair of actuators (104, 106) (or "firing knobs") pivotably coupled to slide block (102), and a plurality of elongate beams (108, 112) extending distally from slide block (102). A pair of side beams (108) are coupled at their proximal ends to a distal end of slide block (102) and terminate distally in a pair of cam ramps (110). Cam ramps (110) are configured to engage the undersides of staple drivers housed within staple cartridge (130) and actuate staple drivers upwardly to thereby drive (or "fire") staples from cartridge (130) into tissue clamped between staple cartridge (130) and anvil plate (72). A center beam (112) is coupled with side beams (108) via a bridge member (114) (or "knife block") spaced distally from slide block (102). Center beam (112) terminates distally in a distally angled knife member (116) having a distal cutting edge (118) configured to cut tissue clamped between the distal portions of stapler halves (12, 14). A distal portion of center beam (112) additionally includes an upwardly projecting stop element (120) proximal to knife member (116), and a distally facing lockout projection (122) proximal to stop element (120).

Each actuator (104, 106) of firing assembly (100) is configured and rotatable relative to slide block (102) between a deployed position and a retracted position such that only one actuator (104, 106) may be deployed at a time, for example as described in greater detail in U.S. Pat. Pub. No. 2020/0046350, issued as U.S. Pat. No. 10,898,187 on Jan. 26, 2021, incorporated by reference above. In the deployed position, an actuator (104, 106) may be driven distally by an operator to actuate firing assembly (100) distally through stapler (10) and thereby simultaneously cut and staple tissue clamped between stapler halves (12, 14).

B. Exemplary Use of Linear Surgical Stapler

Figure 5A:
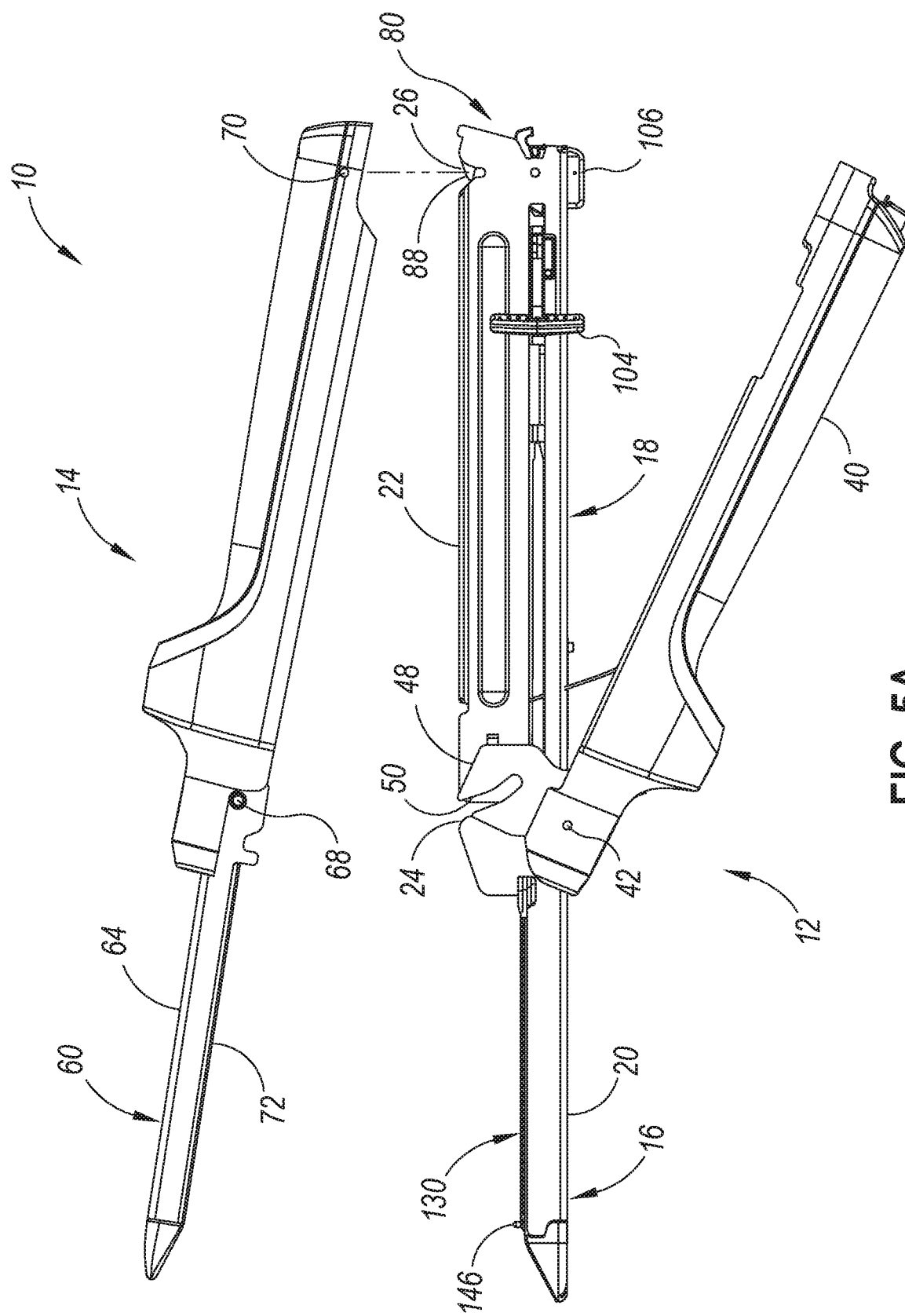
FIG. 5A depicts a side elevational view of the linear surgical stapler of FIG. 1, showing the stapler halves separated from one another.

FIGS. 5A-5E show exemplary coupling of stapler halves (12, 14) and subsequent firing of assembled stapler (10) during a surgical procedure. As shown in FIG. 5A, clamp lever (40) of cartridge half (12) is provided in the open position so that jaw slots (50) align with vertical slots (24) of cartridge channel side flanges (22). Additionally, firing assembly (100) is maintained in its proximal home position by detent member (84) of retaining assembly (80), as shown in FIG. 3 described above. At this stage, a section of tissue (not shown) to be stapled and cut may be positioned over the top of staple cartridge (130) disposed in distal jaw portion (20) of cartridge half (12). Alternatively, the tissue may be positioned over staple cartridge (130) following coupling of the proximal ends of stapler halves (12, 14), described below.

Figure 5B:
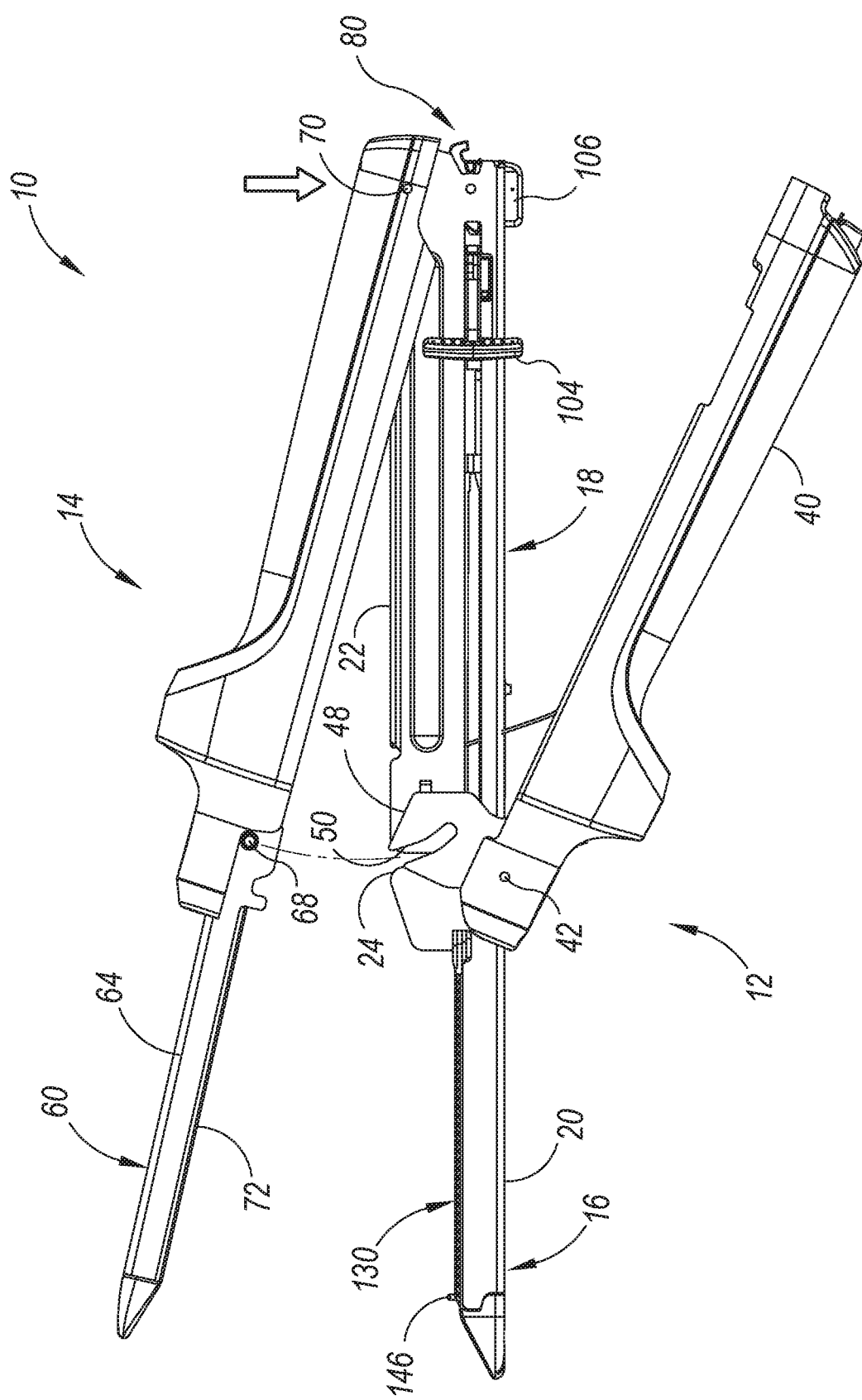
FIG. 5B depicts a side elevational view of the linear surgical stapler of FIG. 1, showing proximal ends of the stapler halves coupled together.
Figure 5C:
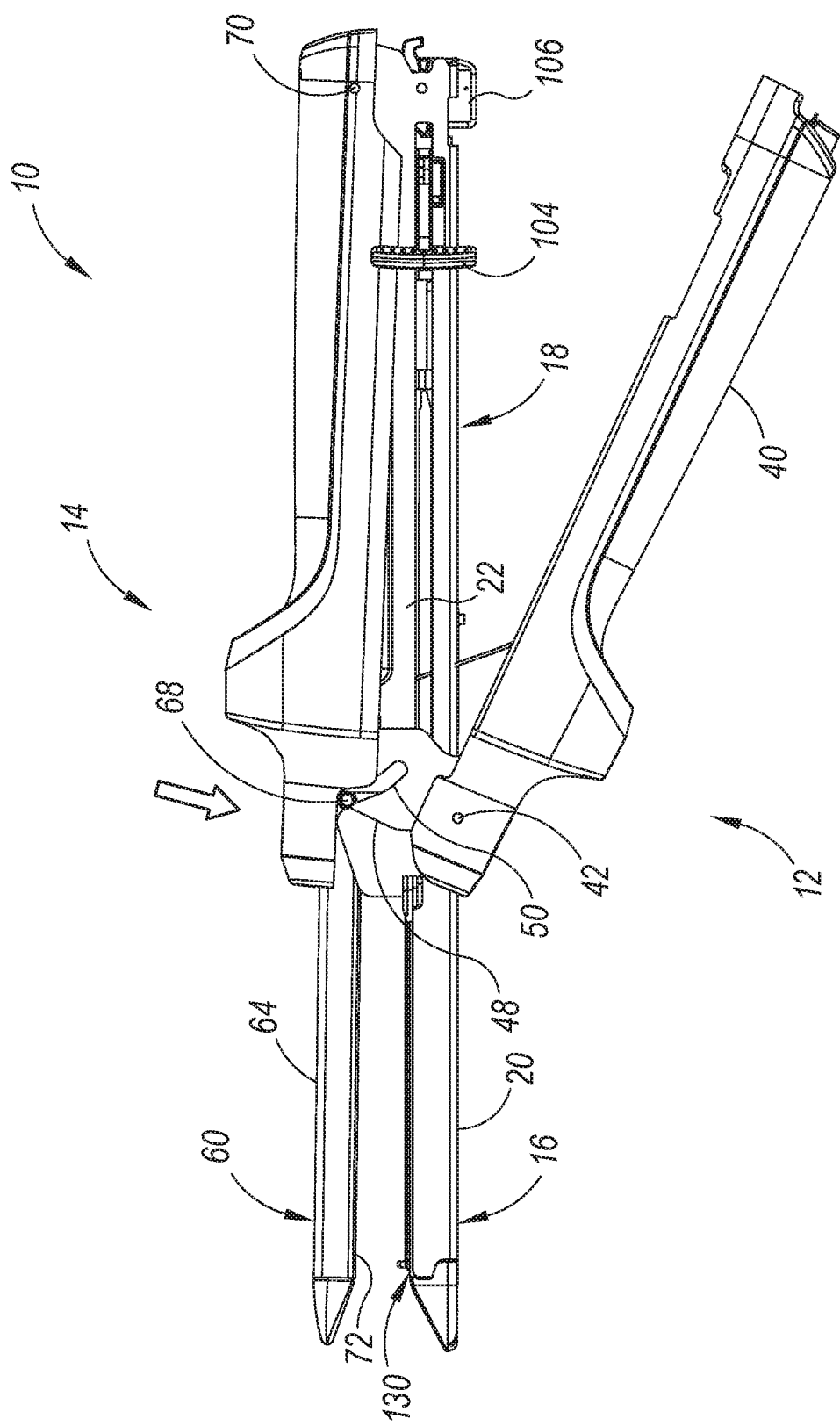
FIG. 5C depicts a side elevational view of the linear surgical stapler of FIG. 1, showing a distal pin of the anvil half being received by clamp lever jaws of the cartridge half.

As shown in FIG. 5A-5B, the proximal ends of stapler halves (12, 14) are aligned with one another and proximal anvil pin (70) is directed downwardly into proximal tapered notches (26) of cartridge channel (16) to engage upper finger (88) of anvil latch member (82). This engagement forces anvil latch member (82) to resiliently rotate clockwise, thus enabling upper finger (88) of anvil latch member (82) to capture anvil pin (70) and thereby releasably couple together the proximal ends of stapler halves (12, 14), as seen in FIG. 5B. As shown in FIG. 5C, and with clamp lever (40) remaining in the open position, anvil half (14) is rotated toward cartridge half (12) about proximal anvil pin (70) so that distal latch pin (68) of anvil half (14) is received into vertical slots (24) of cartridge channel side flanges (22) and jaw slots (50) of clamp lever (40). Distal jaw portions (20, 64) of stapler halves (12, 14) are now in a partially approximated state such that tissue received therebetween may be finally adjusted before clamping.

Figure 5D:
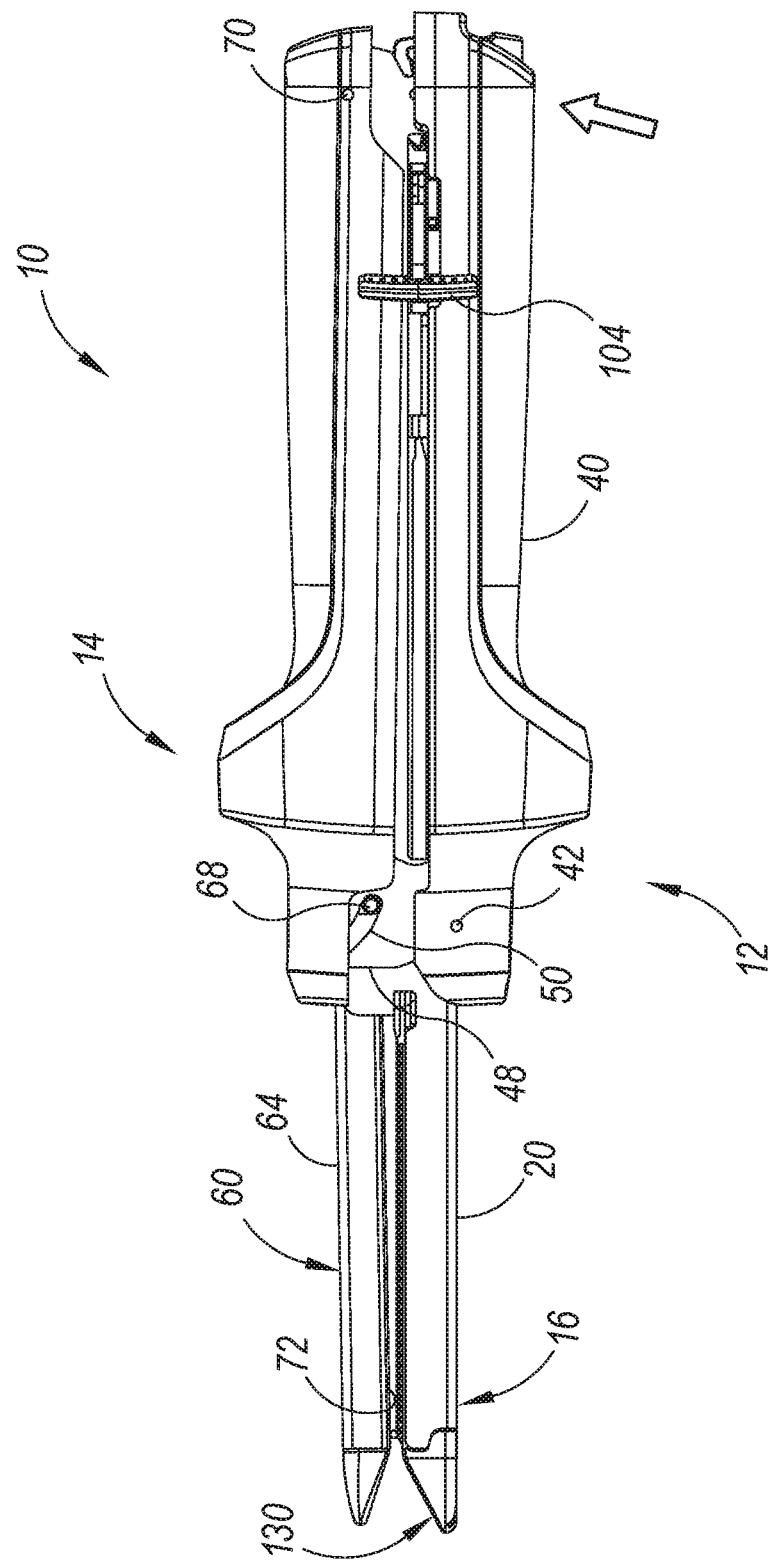
FIG. 5D depicts a side elevational view of the linear surgical stapler of FIG. 1, showing closure of the clamp lever to fully clamp the stapler halves together.

As shown in FIG. 5D, clamp lever (40) is closed to draw anvil latch pin (68) against the closed proximal ends of jaw slots (50) and thereby fully clamp anvil half (14) against cartridge half (12), with tissue (not shown) clamped between staple cartridge (130) and anvil plate (72). A slight transverse gap is defined between staple cartridge (130) and anvil plate (72) by a tissue gap post of staple cartridge (130), thus accommodating the tissue therebetween with a predetermined degree of tissue compression. Tissue gap post is disposed at a distal end of staple cartridge (130) and is configured to contact a distal end of anvil plate (72) when stapler (10) is in the fully clamped state shown in FIG. 5D.

Figure 5E:
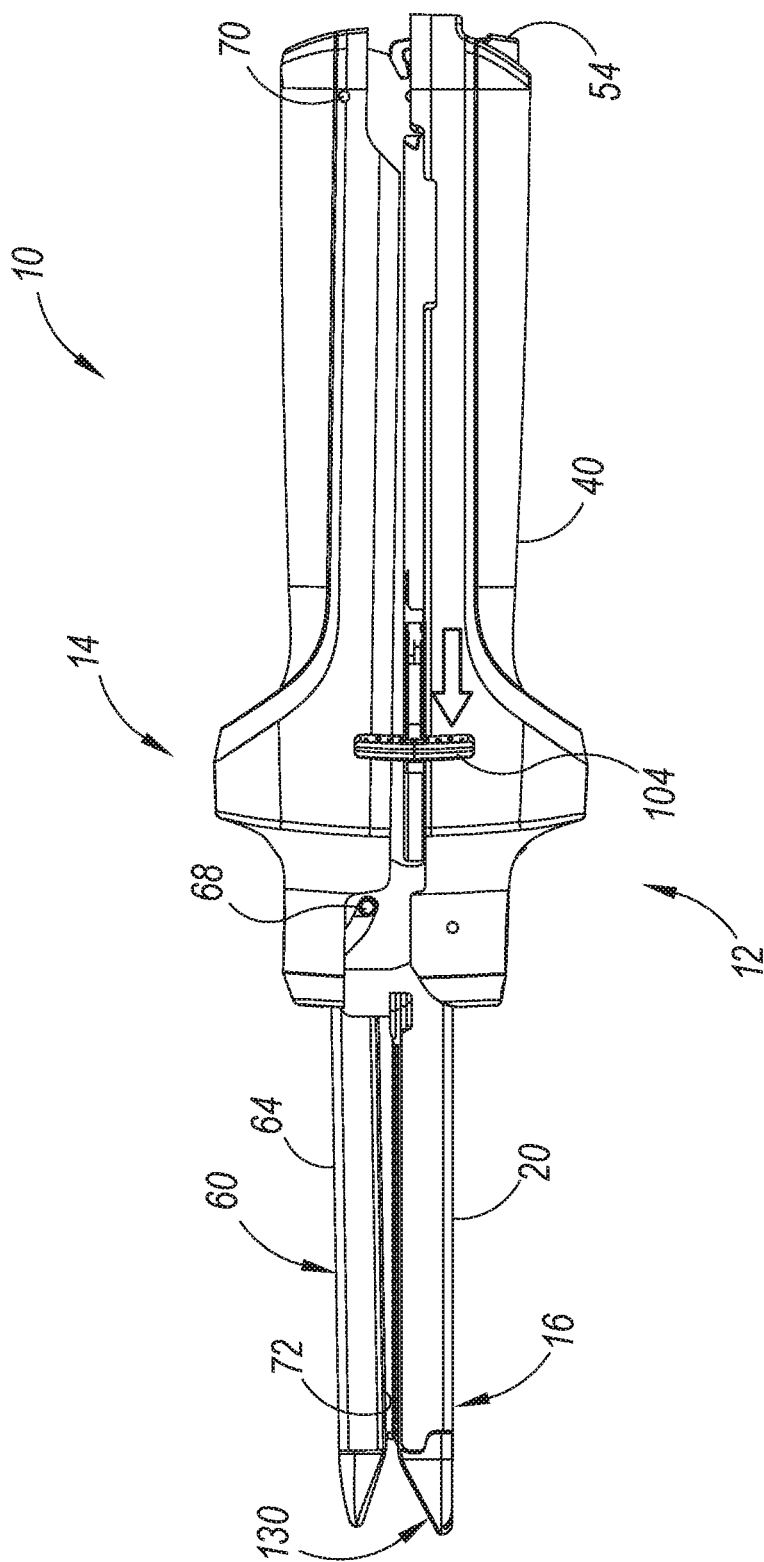
FIG. 5E depicts a side elevational view of the linear surgical stapler of FIG. 1, showing distal actuation of the firing assembly while the stapler halves are in the fully clamped state.

As shown in FIG. 5E, upon reaching the fully clamped state, stapler (10) may be fired by driving a deployed actuator (104, 106) of firing assembly (100) distally along proximal frame portion (18) of cartridge half (12). As described above in connection with FIG. 4, this action causes elongate beams (108, 112) of firing assembly (100) to translate distally through corresponding channels formed in staple cartridge (130) and thereby fire staples into the clamped tissue via cam ramps (110) and staple drivers (180), and simultaneously cut the clamped tissue with knife member (116). Following completion of the firing stroke, firing assembly (100) is returned to its proximal home position via the actuator (104, 106). Clamp lever latch member (54) may then be depressed to release the proximal end of clamp lever (40) from cartridge channel (16), thus permitting clamp lever (40) to be re-opened. Then, release button (90) of retaining assembly (80) may be depressed to release anvil half (14) from cartridge half (12) so that stapler halves (12, 14) may be separated from one another, thereby releasing the newly stapled and severed tissue. It will be understood that in some versions, stapler (10) may include features that promote decoupling of stapler halves (12, 14) similar to those features disclosed in U.S. Pat. Pub. No. 2020/0046351, issued as U.S. Pat. No. 11,033,266 on Jun. 15, 2021, incorporated by reference above.

II. Exemplary Linear Surgical Stapler with Alternative Separation Mechanisms

As mentioned above, and as shown between FIGS. 5A-5B, proximal anvil pin (70) of anvil half (14) is configured to be received within proximal tapered notches (26) of cartridge channel (16) in order to selectively pivotally couple anvil half (14) relative to cartridge half (12) about the lateral axis defined by proximal anvil pin (70). As shown between FIGS. 5B-5C, this pivotal coupling between anvil half (14) and cartridge half (12) allows the operator to rotate anvil half (14) toward cartridge half (12) about proximal anvil pin (70) so that distal latch pin (68) of anvil half (14) is received into vertical slots (24) of cartridge channel side flanges (22) and jaw slots (50) of clamp lever (40).

As also mentioned above, anvil latch member (82) of retaining assembly (80) is configured to capture anvil pin (70) within tapered notches (26) such that after anvil pin (70) is received within notches (26), the operator may focus on rotating anvil half (14) toward cartridge half (12) into the position shown in FIG. 5C without having to worry about anvil pin (70) incidentally dissociating with tapered notches (26), thereby inadvertently decoupling anvil half (14) and cartridge half (14).

However, in some instances, it may not be possible or desirable to have a cartridge half (12) with retaining assembly (80) configured to selectively capture anvil pin (70) within tapered notches (26), thereby temporarily securing the pivotal coupling of stapler (10) about the axis defined by anvil pin (70). In instances where stapler (10) is without anvil latch member (82) as described above, the temporary pivotal coupling of cartridge half (12) with anvil half (14) via anvil pin (70) and tapered notches (26) may be prone to accidental decoupling when the operator attempts to suitably manipulate stapler (10) between the positions shown in FIGS. 5B-5C. For instance, while stapler (10) is in the position shown in FIG. 5B, if the operator is attempting to suitably manipulate cartridge half (12) without holding anvil half (14), anvil pin (70) may fall out of the confines of tapered notches (26), thereby inadvertently decoupling cartridge half (12) with anvil half (14).

Therefore, it may be desirable for a stapler (10) to have a temporary proximal coupling between anvil half (14) and cartridge half (12) that also ensures a secure proximal pivotal relationship between halves (12, 14), while also allowing for intuitive and easy alignment, assembly, and disassembly of halves (12, 14).

A. First Linear Surgical Stapler with Resilient Latch Separation Mechanism

FIGS. 6-11 show an exemplary linear surgical stapler (210) that may be used in replacement of linear surgical stapler (10) described above. As will be described in greater detail below, linear surgical stapler (210) include a latching proximal coupling assembly (270) that allows for easy coupling and decoupling of a cartridge half (212) and an anvil half (214) while ensuring a secure proximal pivotal relationship between halves (212, 214).

Linear surgical stapler (210) may be substantially similar to linear surgical stapler (10) described above, with differences elaborated below. Therefore, linear surgical stapler (212) includes cartridge half (212) and anvil half (214), which are substantially similar to cartridge half (12) and anvil half (14), described above, with differences elaborated below.

Cartridge half (212) includes an elongate cartridge channel (216), a proximal frame (218) having upright side flanges (222), a firing assembly (230), and a clamp lever (240) having an elongate arm (244) and a pair of opposed jaws (248); which are substantially similar to elongate cartridge channel (16), proximal frame (18), upright side flanges (22), firing assembly (100), clamp lever (40), elongate arm (44), and opposed jaws (48) described above, respectively, with differences elaborated below.

Anvil half (214) includes an elongate anvil channel (260), a proximal frame portion (262), a distal jaw portion (264), a latch pin (268), and a shroud (278); which are substantially similar to elongate anvil channel (60), proximal frame portion (62), distal jaw portion (64), latch pin (68), and shroud (78) described above, respectively, with differences elaborated below.

While cartridge half (12) and anvil half (14) include tapered notches (26) and proximal pin (70), respectively, in order to provide a temporary pivotal coupling between cartridge half (12) and anvil half (14); linear surgical stapler (210) includes latching proximal coupling assembly (270) that allows for temporary coupling between cartridge half (212) and anvil half (214) while also ensuring a secure proximal pivotal relationship between halves (212, 214).

Figure 9:
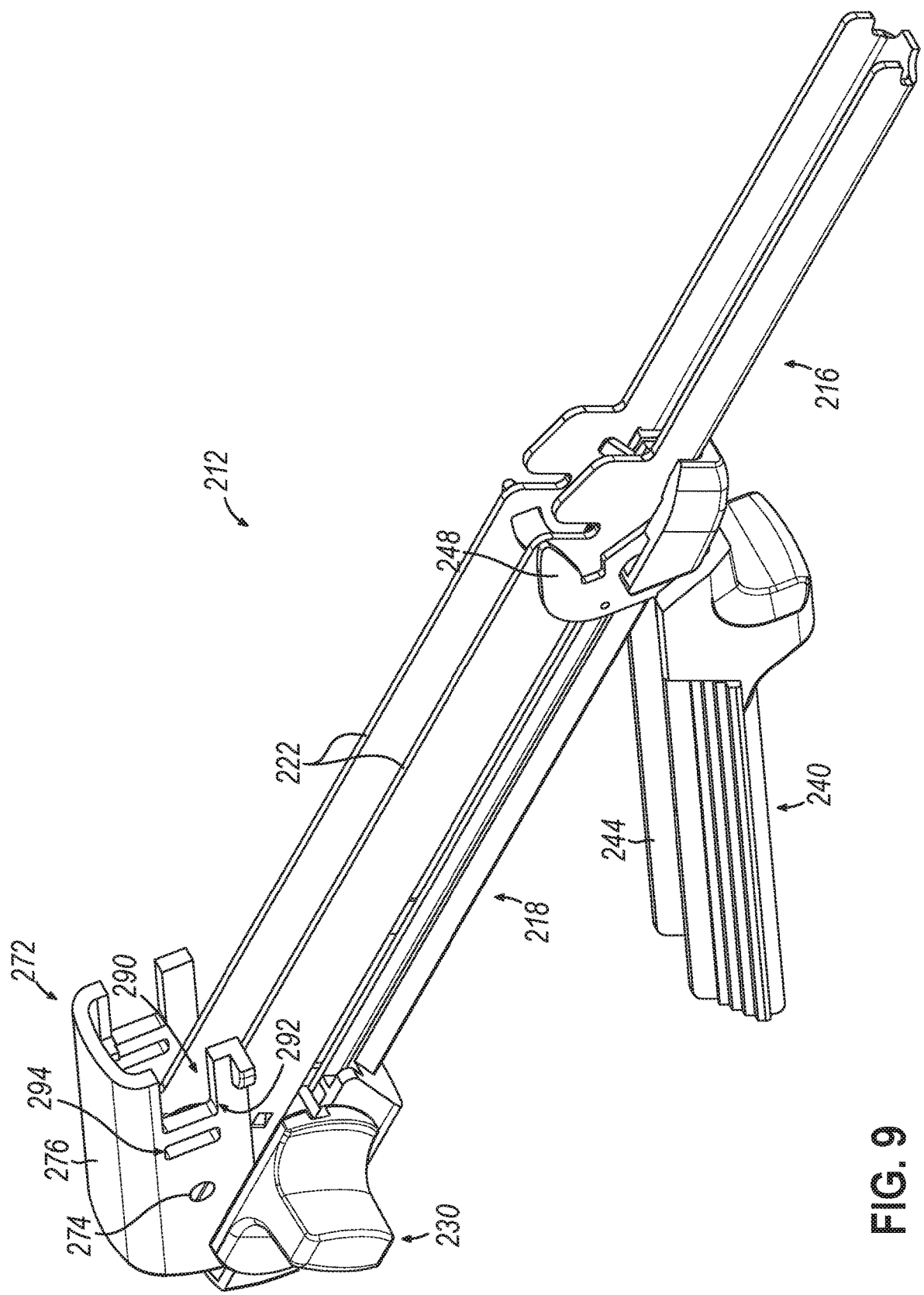
FIG. 9 depicts a perspective view of the cartridge half of FIG. 6.

Latching proximal coupling assembly (270) includes a pivoting cartridge section (272) and an anvil coupling section (280). As best shown in FIG. 9, pivoting cartridge section (272) includes a pivot pin (274) and a pivot housing (276). Pivot housing (276) is pivotally coupled with a proximal section of proximal frame portion (218) via pivot pin (274) associated with side flanges (222).

Unlike proximal pin (70) described above, pivot pin (274) is configured to remain pivotably coupled with side flanges (222) such that during exemplary use, pivot pin (274) and pivot housing (276) may not disassociate with proximal frame portion (218). In other words, pivot housing (276) is attached to side flanges (222) such that pivot housing (276) may pivot relative to proximal frame (218) about the axis defined by pivot pin (274), but pivot housing (276) may not otherwise detach or disassociate with proximal frame portion (218) during exemplary use. For example, if the operator held cartridge half (212) solely by grasping pivot housing (276), pivot housing (276) and proximal frame portion (218) will remain coupled via interaction between pivot pin (274) and side flanges (222).

Pivot housing (276) defines a hollow interior (290); while side walls of pivot housing (276) define a distally presented open slot (292) and a latch aperture (294). Hollow interior (290) is dimensioned to selectively house a proximal section of proximal frame portion (262) and anvil coupling section (280). As will be described in greater detail below, pivot housing (276) is configured to selectively couple with anvil half (214) via anvil coupling section (280) in order to establish a secure pivotably coupling between anvil half (214) and proximal frame portion (218).

Figure 10:
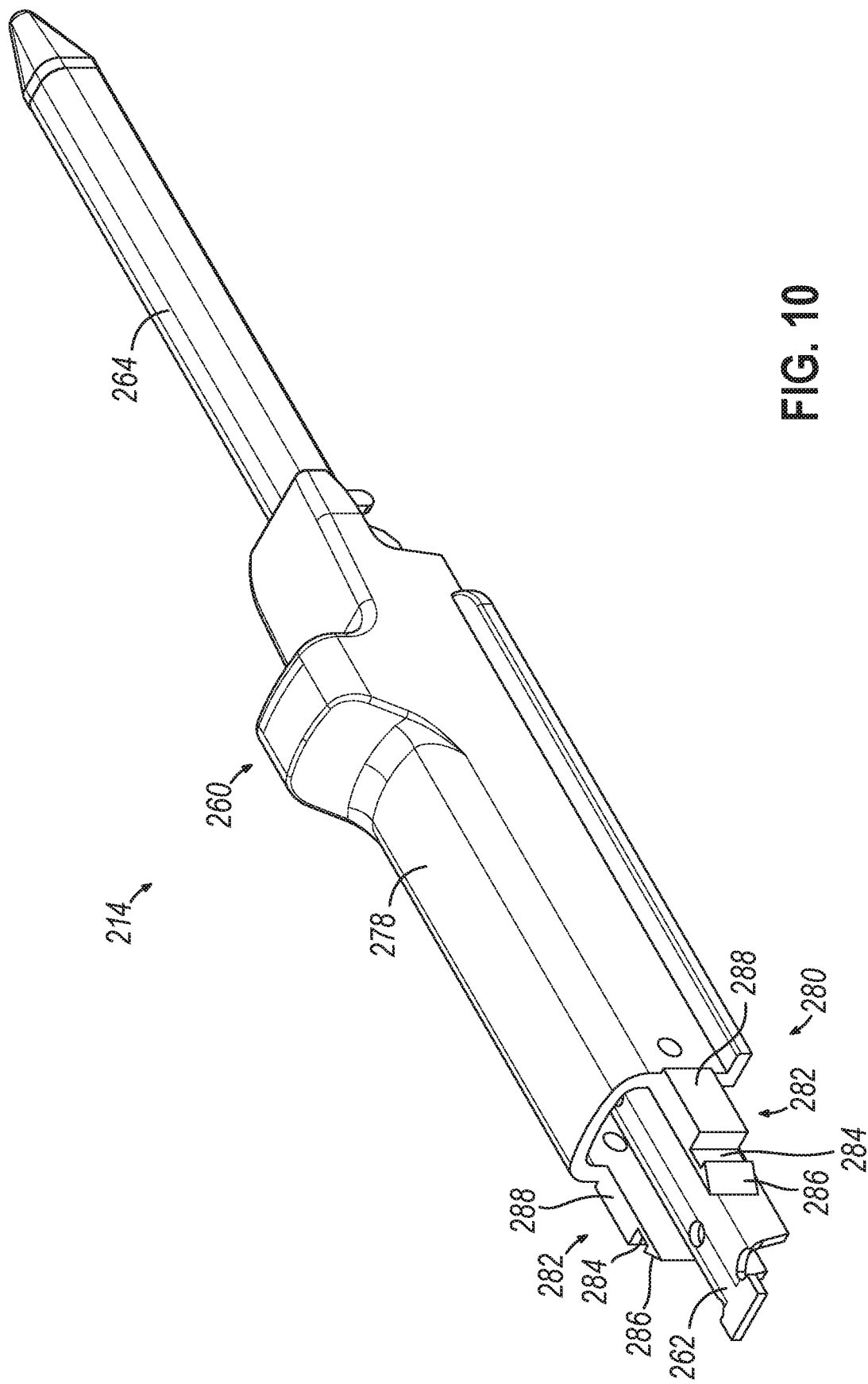
FIG. 10 depicts a perspective view of the anvil half of FIG. 6.
Figure 11:
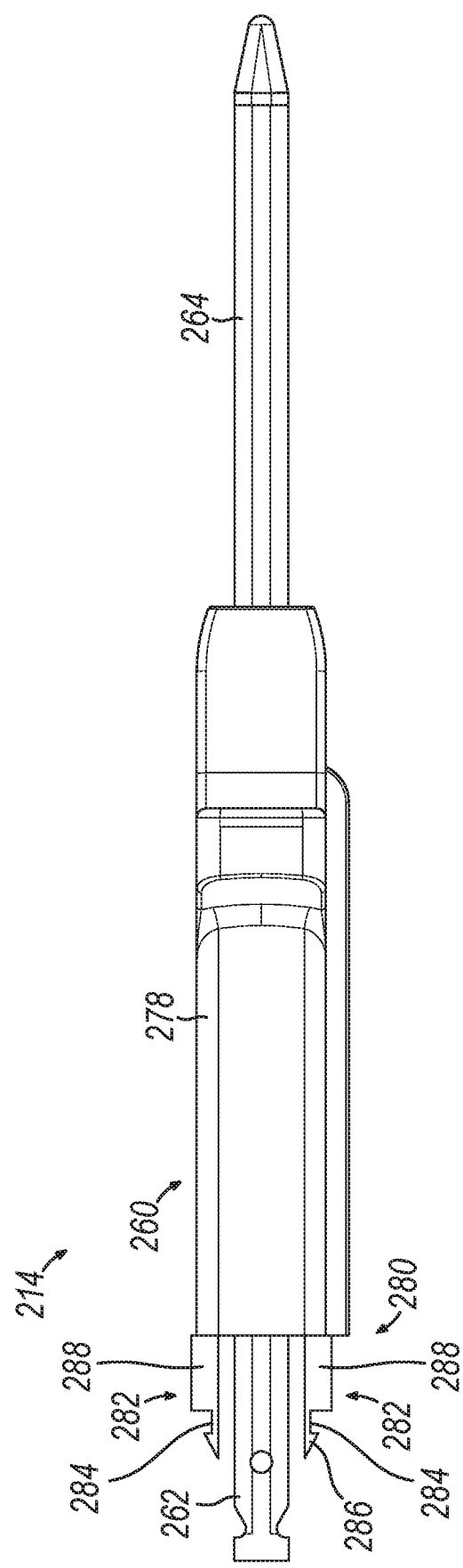
FIG. 11 depicts a top plan view of the anvil half of FIG. 6.

As best shown in FIGS. 10-11, anvil coupling section (280) includes a pair of stability blocks (288) extending proximally from a respective side of shroud (278) and a pair of resilient latches (282) extending proximally from a respective stability block (288). Stability blocks (288) are dimensioned to fit within the confines of a respective distally presented open slot (292) of pivoting cartridge section (272) when anvil coupling section (280) is attached to pivoting cartridge section (272) in accordance with the description herein.

Resilient latches (282) each include a leg (284) extending proximally from respective stability block (288), which terminates into a latch head (286). Latch heads (286) include a slanted camming surface and an engagement shoulder. Latch heads (286) are dimensioned to fit within a respective latch aperture (294) when anvil coupling section (280) is attached to pivoting cartridge section (272). Legs (284) are sufficiently resilient to flex to accommodate coupling of anvil coupling section (280) with pivoting cartridge section (272) in accordance with the description herein.

Figure 6:
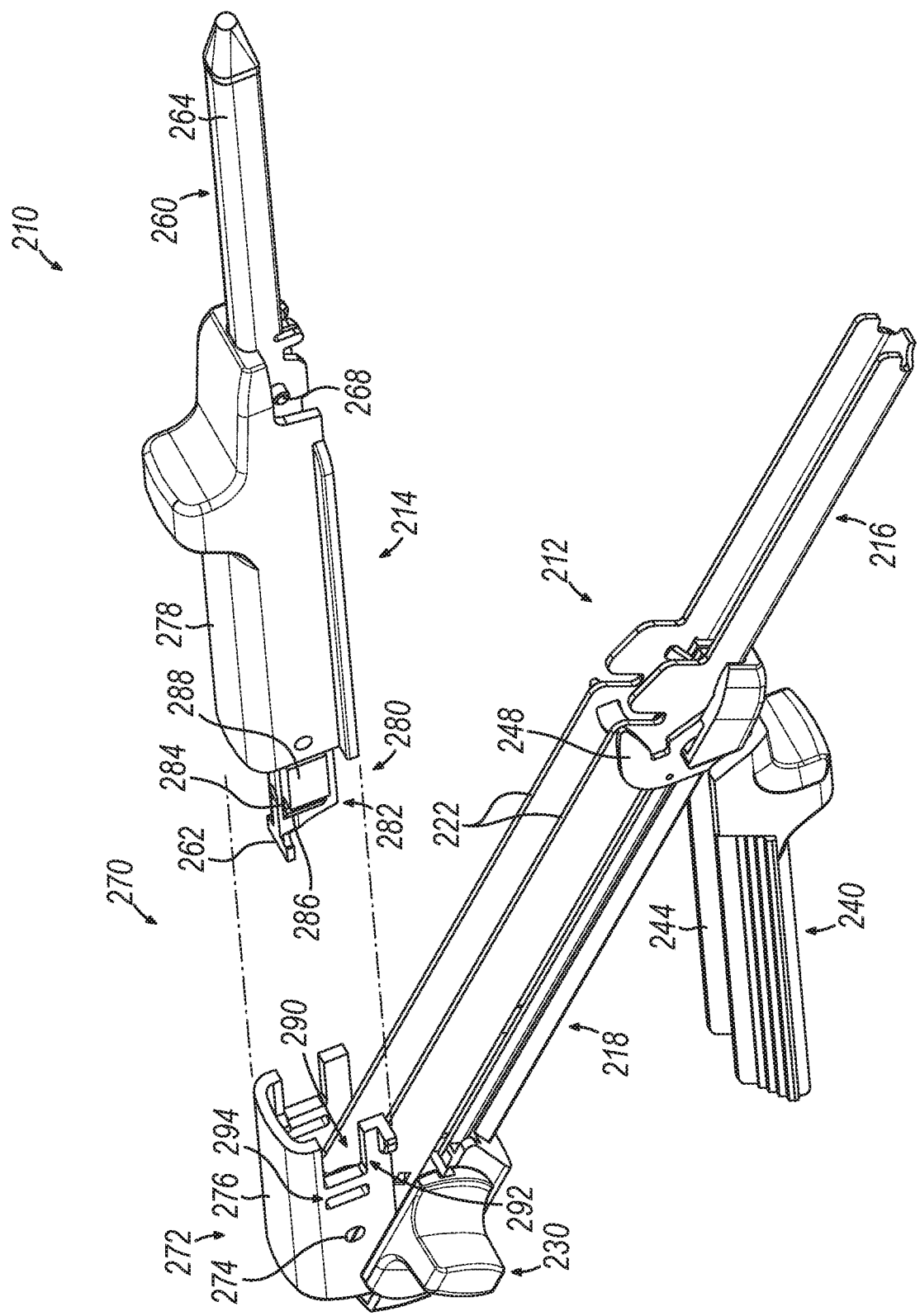
FIG. 6 depicts a perspective view of an alternative linear surgical stapler, showing a cartridge half and an anvil half of the stapler separated from each other with a clamp lever of the cartridge half in an open position.
Figure 7:
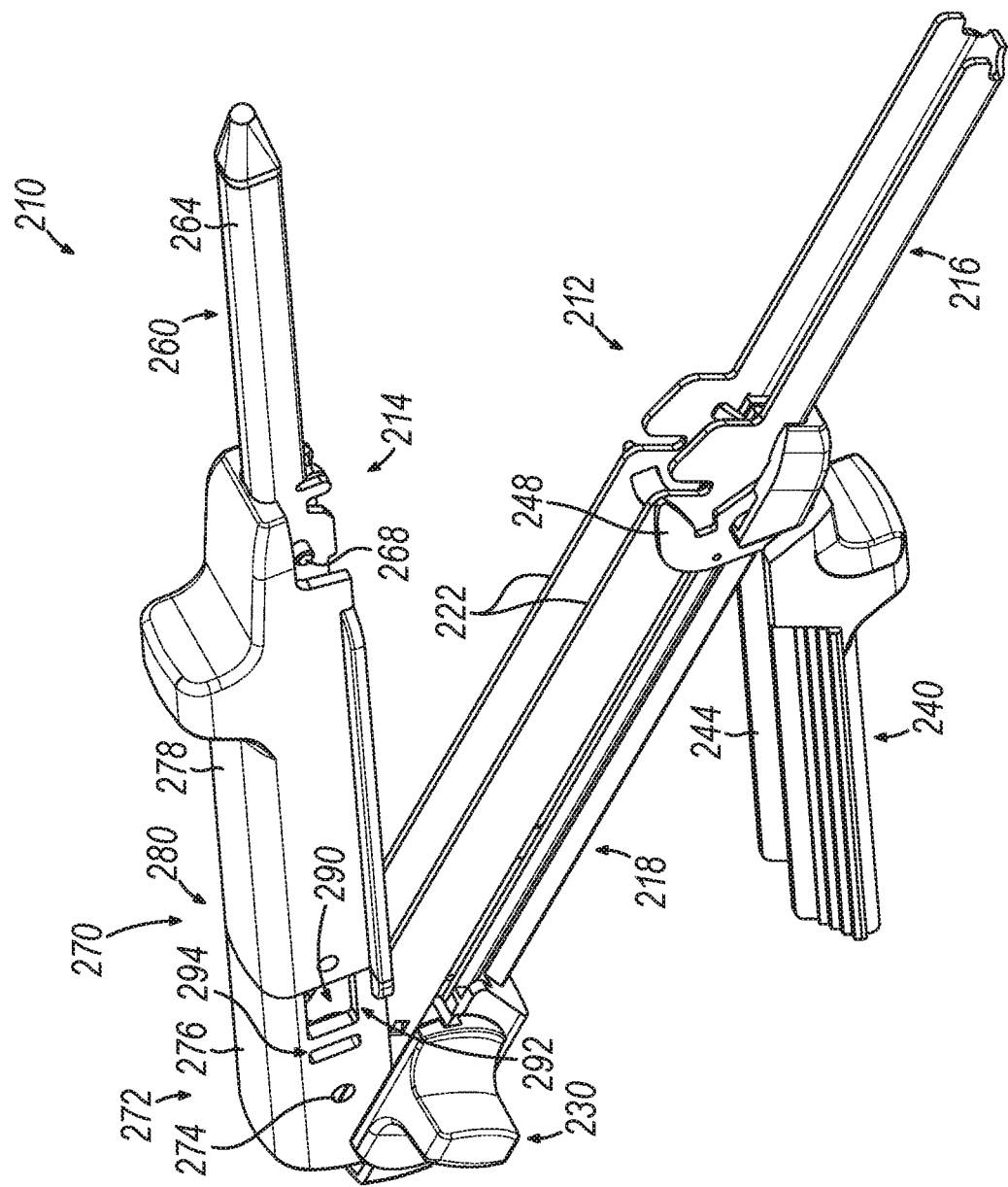
FIG. 7 depicts a perspective view of the linear surgical stapler of FIG. 6, showing the cartridge half and the anvil half of the stapler coupled together with the clamp lever of the cartridge half in the-open position.
Figure 8:
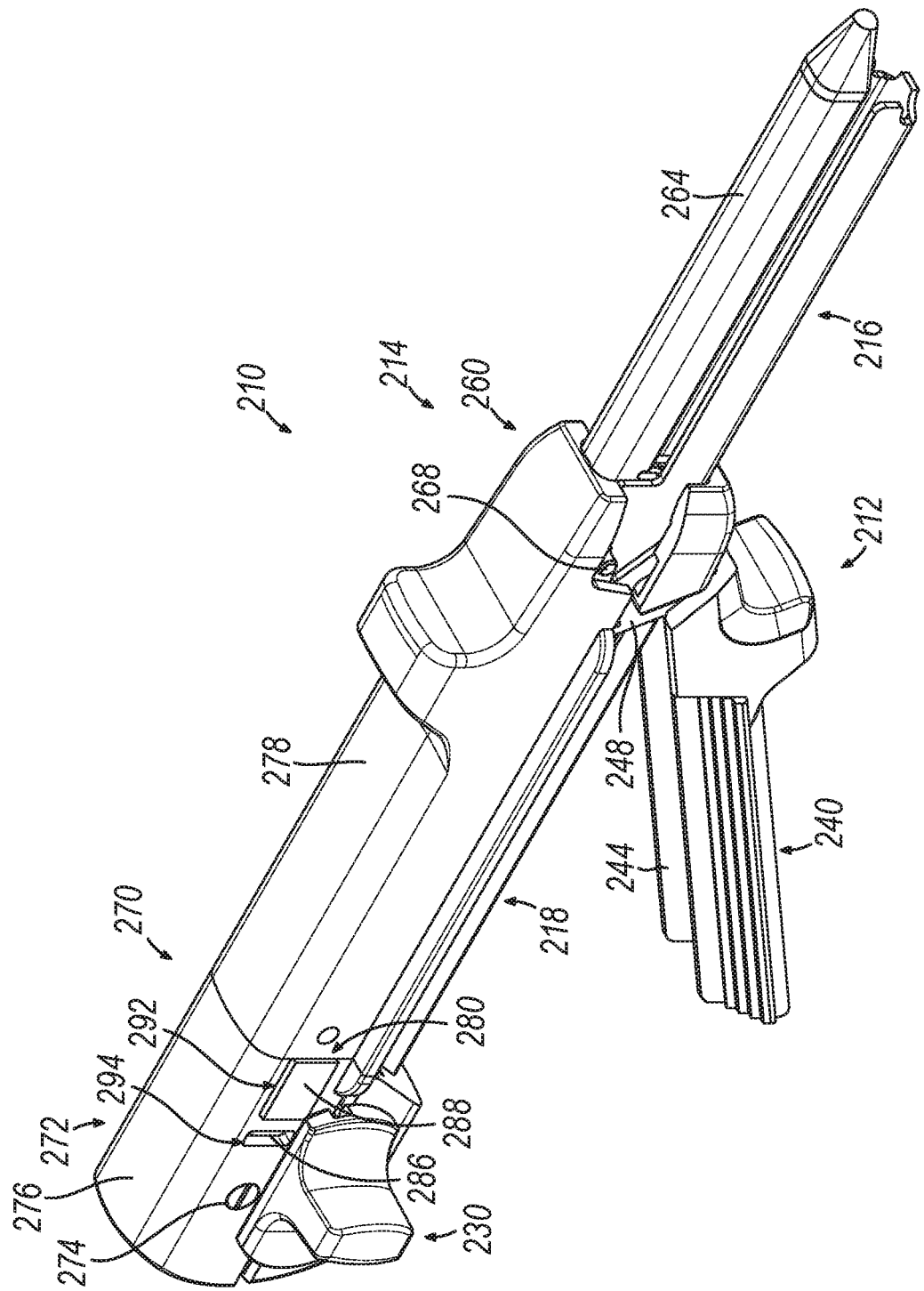
FIG. 8 depicts a perspective view of the linear surgical stapler of FIG. 6, showing a distal pin of the anvil half being received by clamp lever jaws of the cartridge half.

FIGS. 6-8 show an exemplary assembly of anvil half (214) with cartridge half (212) via proximal coupling assembly (270). First, as shown in FIG. 6, the operator may align the open end of pivot housing (276) with the proximal end of anvil coupling section (280). Next, as shown between FIGS. 6-7, the operator may insert anvil coupling section (280) into hollow interior (290) of pivot housing (276).

Legs (284) are sufficiently resilient in order to flex in response to camming surface of latch head (286) engaging an interior surface of pivot housing (276) while the operator inserts anvil coupling section (280) into hollow interior (290) of pivot housing (276). Additionally, once in the position shown in FIG. 7, legs (284) are sufficiently resilient to return to a relaxed position when latch heads (286) are aligned with latch aperture (284). When legs (284) returns to the relaxed position, latch heads (286) may be housed within their respective latch aperture (284). At the moment shown in FIG. 7, anvil coupling section (280) is fully inserted within hollow interior (290).

Once latch heads (286) are housed within latch apertures (284), engagement shoulders of latch heads (286) may inhibit distal longitudinal motion of anvil half (214) relative to pivot housing (276). Additionally, engagement between stability blocks (288) and their respective distally presented open slot (292) may be sufficient to prevent lateral or rotational motion between anvil half (214) and pivot housing (276). Therefore, once suitably inserted into pivot housing (276), anvil half (214) may be sufficiently attached to pivot housing (276) such that anvil half (214) is also pivotally coupled to proximal frame (218) of cartridge half (212).

Since pivot housing (276) has a secure pivotal coupling with proximal frame portion (218), as described above, anvil half (214) also has a secure pivotal coupling when coupled to pivot housing (276) via anvil coupling section (280). Therefore, due to the secure pivotal coupling, the operator may attempt to suitably manipulate stapler (210) between the positions shown in FIGS. 7-8 without halves (212, 214) inadvertently decoupling at a proximal pivotal coupling.

The operator may then utilize stapler (210) in accordance with the description herein. When the operator desires to decouple halves (212, 214), the operator may pinch stability blocks (288) inward, or otherwise actuate latch heads (286) into their respective latch aperture (284) such that engagement shoulders no longer engage the portion of pivot housing (276) defining latch apertures (284). Simultaneously, the operator may pull anvil half (214) away from pivot housing (276) until anvil coupling section (280) is entirely removed from hollow interior (290) of pivot housing (276).

Figure 12:
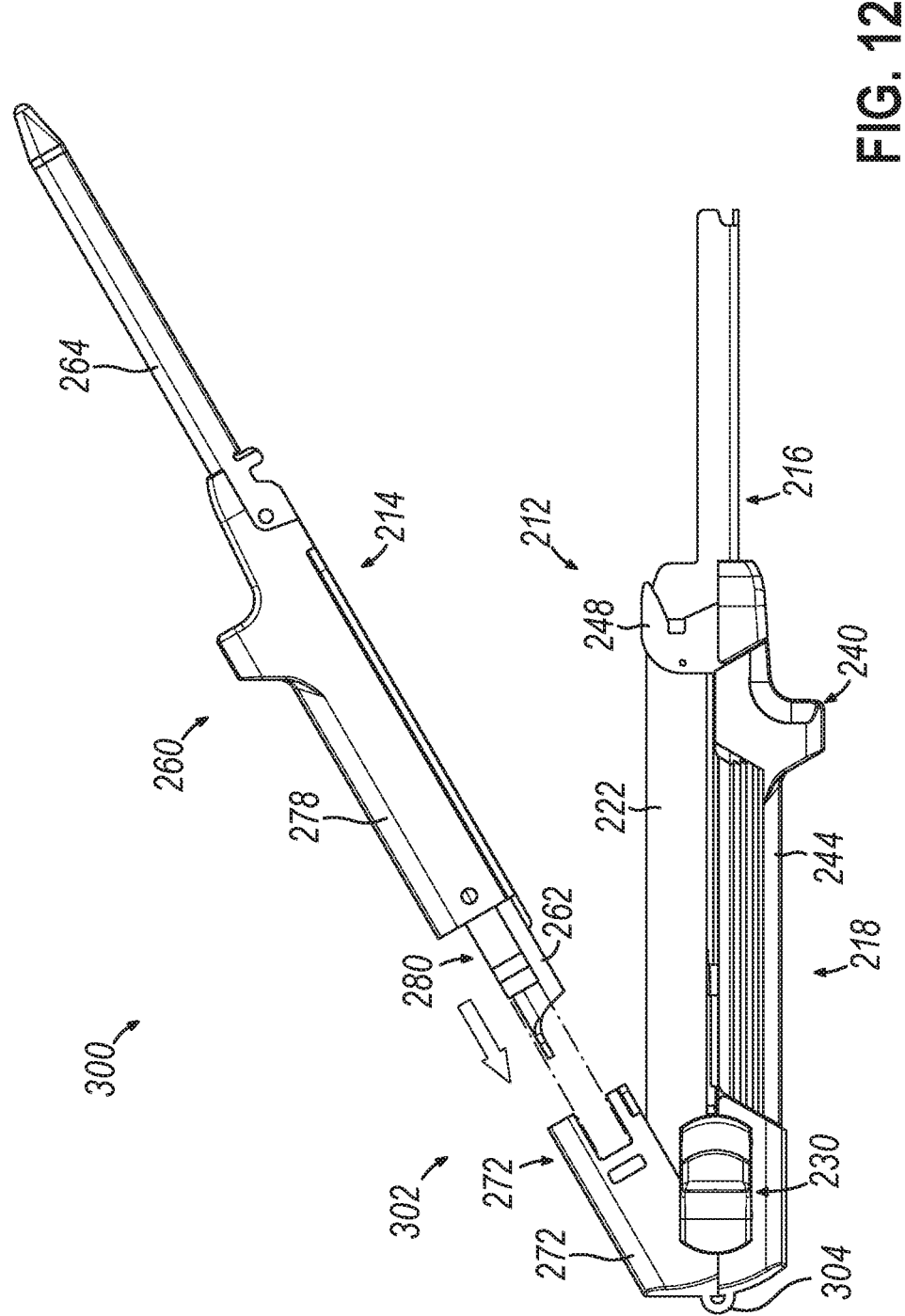
FIG. 12 depicts an elevational side view of an alternative linear surgical stapler, showing a cartridge half and an anvil half of the stapler separated from each other.

While in the current example, pivot pin (274) and side flanges (222) pivotally couple proximal frame portion (218) and pivot housing (276), any other suitable mechanism may be used to pivotally couple pivot housing (276) with proximal frame portion (218) as would be apparent to one skilled in the art in view of the teachings herein. For example, as shown in FIG. 12, pivot housing (276) may be pivotally couple with proximal frame portion (218) via living hinge (304), thereby forming a linear stapler (300) with a proximal coupling assembly (302) that is substantially similar to linear surgical stapler (210) and proximal coupling assembly (270), except for the use of living hinge (304) rather than pivot pin (274).

While in the current example, pivot housing (276) associated with the cartridge half (212), this is merely optional, as pivot housing (276) may associate with anvil half (214) and anvil coupling section (280) may associate with cartridge half (212).

B. Second Linear Surgical Stapler with Resilient Latch Separation Mechanism

FIGS. 13-18 show an exemplary linear surgical stapler (310) that may be used in replacement of linear surgical stapler (10) described above. As will be described in greater detail below, linear surgical stapler (310) include a proximal coupling assembly (370) that allows for easy coupling and decoupling of a cartridge half (312) and an anvil half (314) while ensuring a secure proximal pivotal relationship between halves (312, 314).

Linear surgical stapler (310) may be substantially similar to linear surgical stapler (10) described above, with differences elaborated below. Therefore, linear surgical stapler (312) includes cartridge half (312) and anvil half (314), which are substantially similar to cartridge half (12) and anvil half (14), described above, with differences elaborated below.

Cartridge half (312) includes an elongate cartridge channel (316), a proximal frame (318) having upright side flanges (322), a firing assembly (330), and a clamp lever (340) having an elongate arm (344) and a pair of opposed jaws (348); which are substantially similar to elongate cartridge channel (16), proximal frame (18), upright side flanges (22), firing assembly (100), clamp lever (40), elongate arm (44), and opposed jaws (48) described above, respectively, with differences elaborated below.

Anvil half (314) includes an elongate anvil channel (360), a proximal frame portion (362), a distal jaw portion (364), a latch pin (368), and a shroud (378); which are substantially similar to elongate anvil channel (60), proximal frame portion (62), distal jaw portion (64), latch pin (68), and shroud (78) described above, respectively, with differences elaborated below.

While cartridge half (12) and anvil half (14) include tapered notches (26) and proximal pin (70), respectively, in order to provide a temporary pivotal coupling between cartridge half (12) and anvil half (14); linear surgical stapler (310) includes a proximal coupling assembly (370) that allows for temporary coupling between cartridge half (312) and anvil half (314) while also ensuring a secure proximal pivotal relationship between halves (312, 314).

Figure 15:
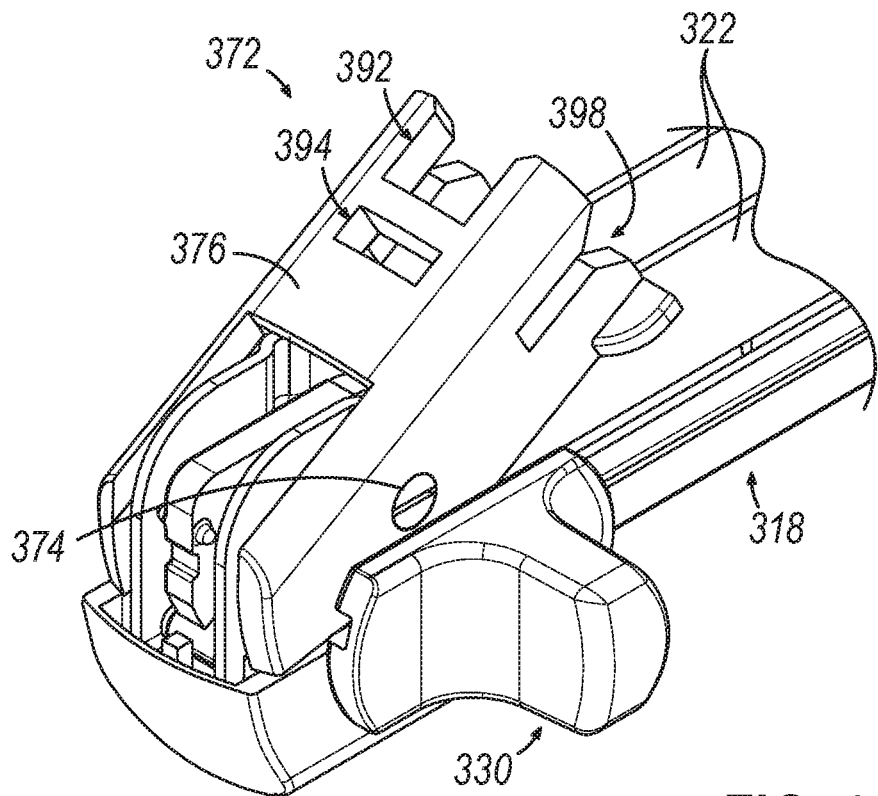
FIG. 15 depicts a perspective view of a proximal portion of the cartridge half of FIG. 13.
Figure 16:
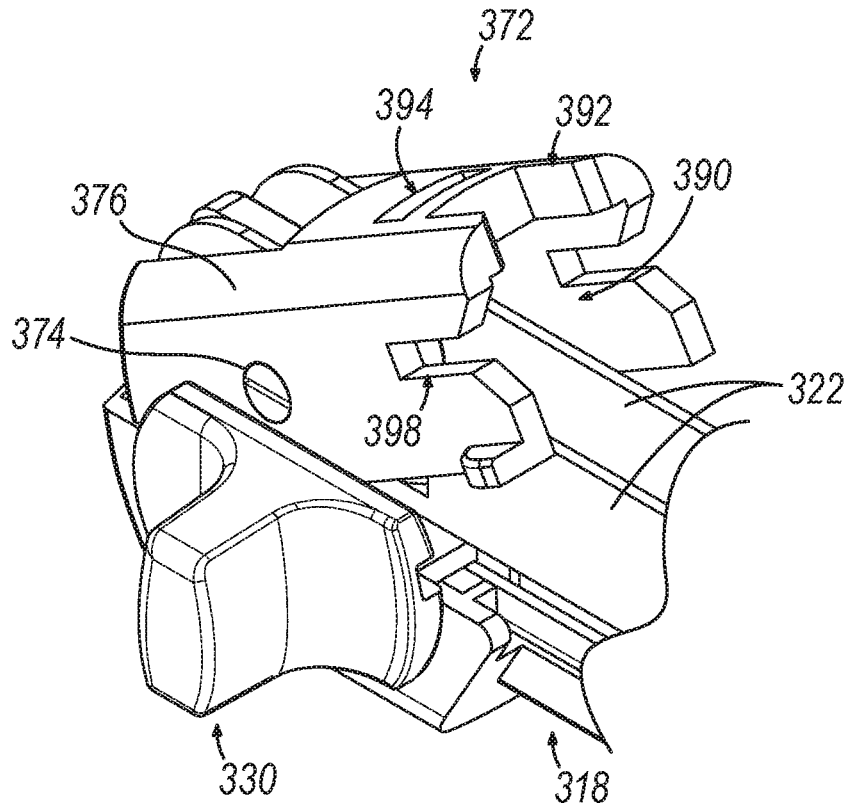
FIG. 16 depicts another perspective view of the proximal portion of the cartridge half of FIG. 13.

Latching proximal coupling assembly (370) includes a pivoting cartridge section (372) and an anvil coupling section (380). As best shown in FIGS. 15-16, pivoting cartridge section (372) includes a pivot pin (374) and a pivot housing (376). Pivot housing (376) is pivotally coupled with a proximal section of proximal frame portion (318) via pivot pin (374) associated with side flanges (322).

Unlike proximal pin (70) described above, pivot pin (374) is configured to remain pivotably coupled with side flanges (322) such that during exemplary use, pivot pin (374) and pivot housing (376) may not disassociate with proximal frame portion (318). In other words, pivot housing (376) is attached to side flanges (322) such that pivot housing (376) may pivot relative to proximal frame (318) about the axis defined by pivot pin (374), but pivot housing (376) may not otherwise detach or disassociate with proximal frame portion (218) during exemplary use. For example, if the operator held cartridge half (312) solely by grasping pivot housing (376), pivot housing (376) and proximal frame portion (318) will remain coupled via interaction between pivot pin (374) and side flanges (322).

Pivot housing (376) defines a hollow interior (390); while a top wall of pivot housing (376) defines a distally presented open slot (392) and a latch aperture (394); and side walls of pivot housing (376) define additional distally presented open slots (398). Hollow interior (390) is dimensioned to selectively house a proximal section of proximal frame portion (362) and anvil coupling section (380). As will be described in greater detail below, pivot housing (376) is configured to selectively couple with anvil half (314) via anvil coupling section (380) in order to establish a secure pivotably coupling between anvil half (314) and proximal frame portion (318).

Figure 17:
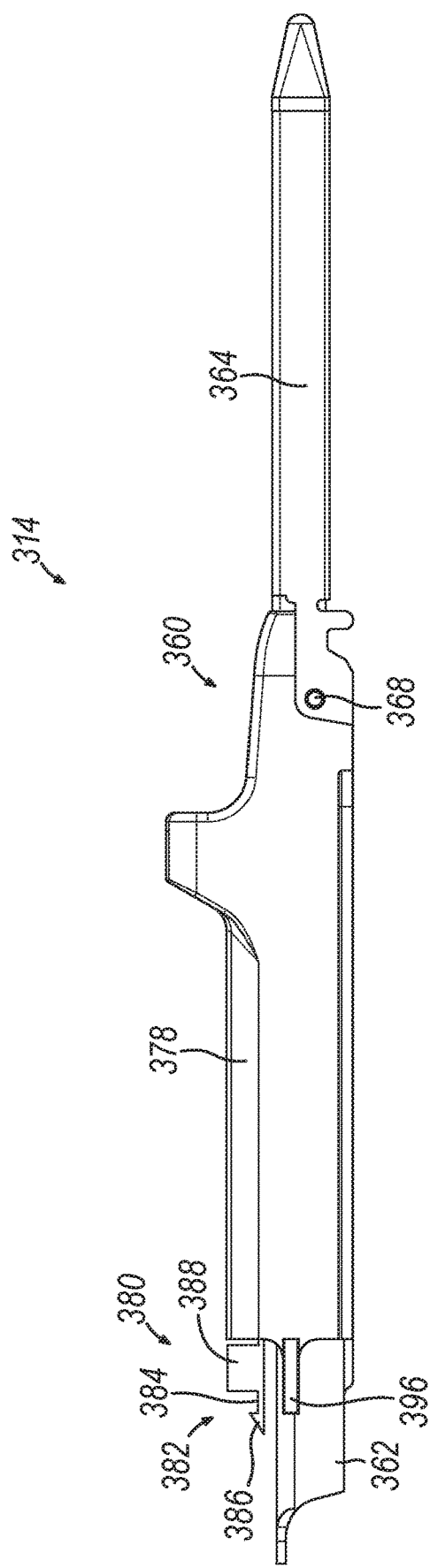
FIG. 17 depicts an elevational side view of the anvil portion of FIG. 13.
Figure 18:
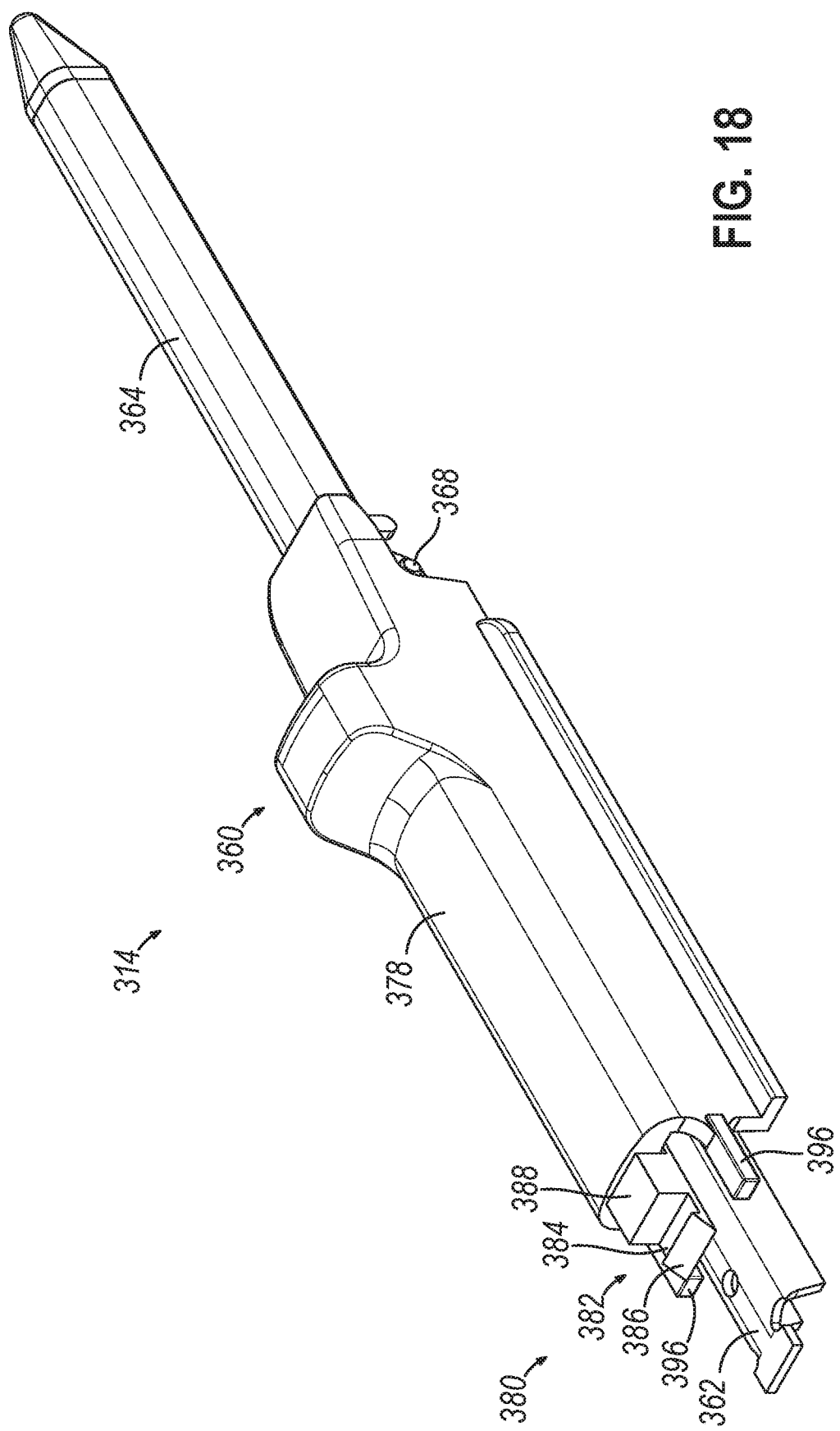
FIG. 18 depicts a perspective view of the anvil portion of FIG. 13.

As best shown in FIGS. 17-18, anvil coupling section (380) includes a stability block (388) extending on the top of, and proximally from shroud (378) and a resilient latch (382) extending proximally from stability block (388). Additionally, anvil coupling section (380) also includes two additional stability blocks (396) extend from the sides on the side, and proximally from shroud (378). Stability blocks (388, 396) are dimensioned to fit within the confines of distally presented open slot (392) and additional distally presented open slots (398), respectively, of pivoting cartridge section (372) when anvil coupling section (380) is attached to pivoting cartridge section (372) in accordance with the description herein.

Resilient latch (382) includes a leg (384) extending proximally from stability block (388), which terminates into a latch head (386). Latch head (386) includes a slanted camming surface and an engagement shoulder. Latch head (386) is dimension to fit within latch aperture (394) when anvil coupling section (380) is attached to pivoting cartridge section (372). Leg (384) is sufficiently resilient to flex to accommodate coupling of anvil coupling section (380) with pivoting cartridge section (372) in accordance with the description herein.

Figure 13:
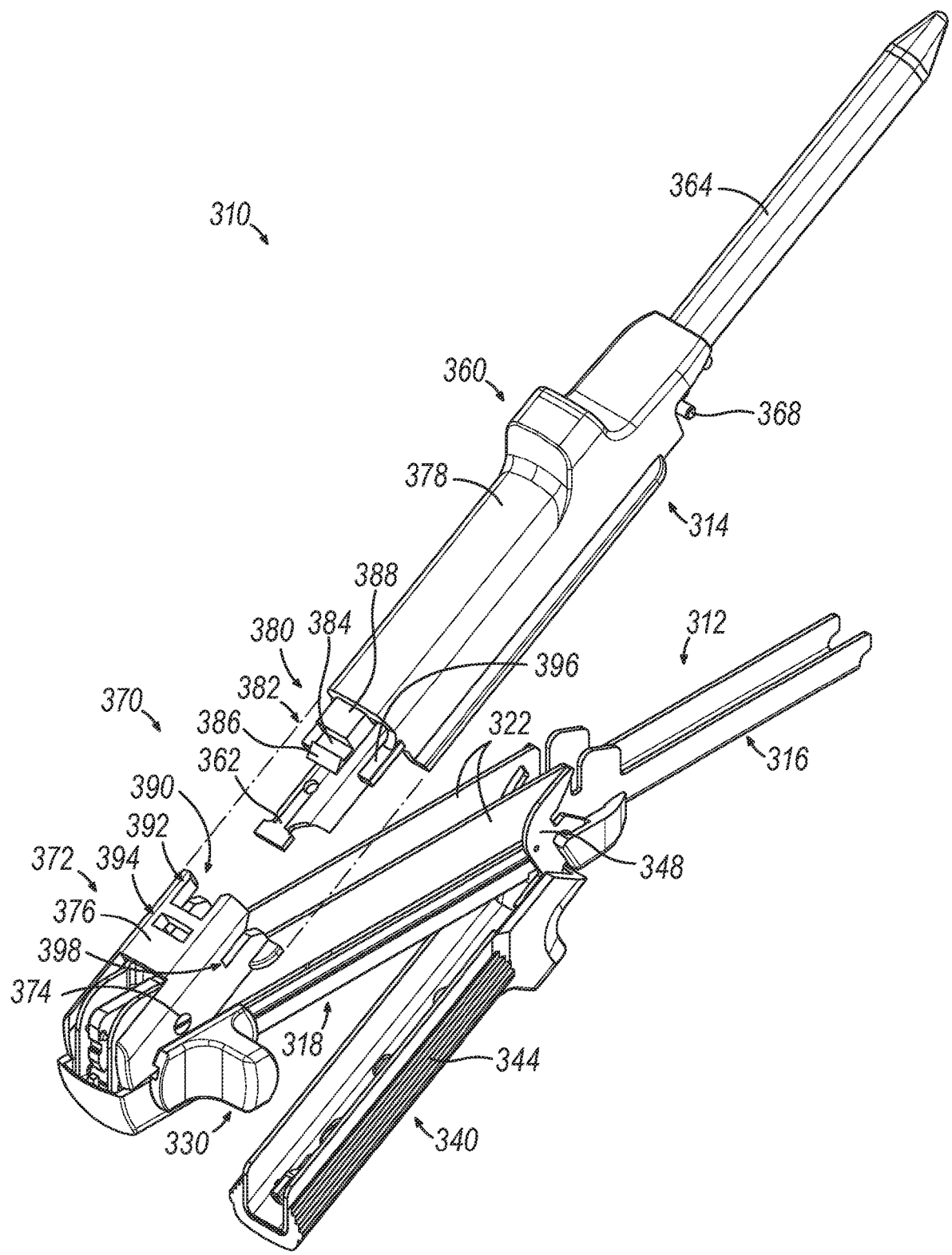
FIG. 13 depicts a perspective view of an alternative linear surgical stapler, showing a cartridge half and an anvil half of the stapler separated from each other with a clamp lever of the cartridge half in an open position.
Figure 14:
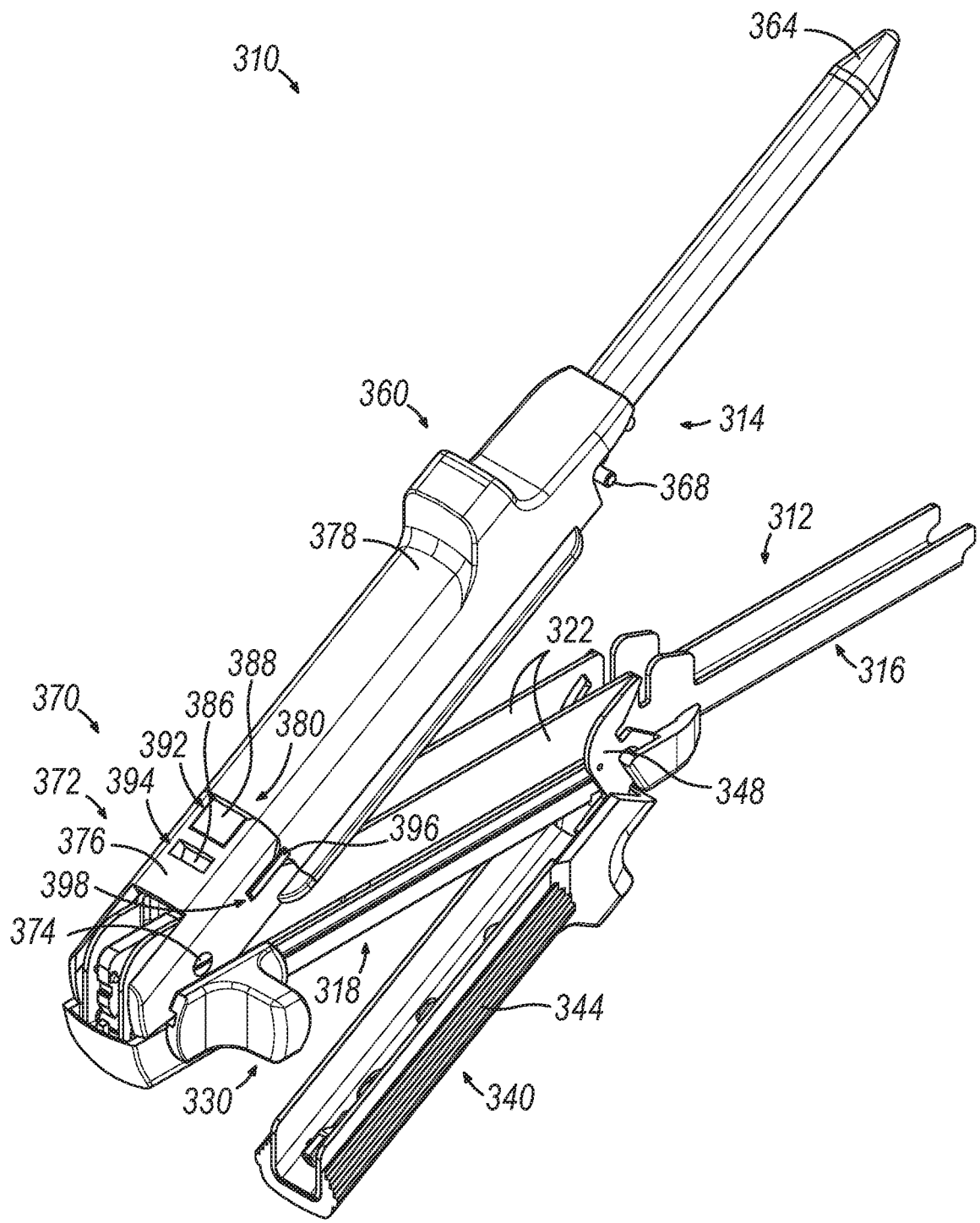
FIG. 14 depicts a perspective view of the linear surgical stapler of FIG. 13, showing the cartridge half and the anvil half of the stapler coupled together with the clamp lever of the cartridge half in the open position.

FIGS. 13-14 show an exemplary assembly of anvil half (314) with cartridge half (312) via proximal coupling assembly (370). First, as shown in FIG. 13, the operator may align the open end of pivot housing (376) with the proximal end of anvil coupling section (380). Next, as shown between FIGS. 13-14, the operator may insert anvil coupling section (380) into hollow interior (390) of pivot housing (376).

Leg (384) is sufficiently resilient in order to flex in response to camming surface of latch head (386) engaging an interior surface of pivot housing (376) while the operator inserts anvil coupling section (380) into hollow interior (390) of pivot housing (376). Additionally, once in the position shown in FIG. 14, leg (384) is sufficiently resilient to return to a relaxed position when latch head (386) is aligned with latch aperture (384). When leg (384) returns to the relaxed position, latch head (386) may be housed within latch aperture (384). At the moment shown in FIG. 14, anvil coupling section (380) is fully inserted within hollow interior (390).

Once latch head (386) is housed within latch aperture (384), engagement shoulder of latch head (386) may inhibit distal longitudinal motion of anvil half (314) relative to pivot housing (376). Additionally, engagement between stability blocks (388, 396) and distally presented open slots (392, 398) may be sufficient to prevent lateral or rotational motion between anvil half (314) and pivot housing (376). Therefore, once suitably inserted into pivot housing (376), anvil half (314) may be sufficiently attached to pivot housing (376) such that anvil half (314) is also pivotally coupled to proximal frame (318) of cartridge half (312).

Since pivot housing (376) has a secure pivotal coupling with proximal frame portion (318), as described above, anvil half (314) also has a secure pivotal coupling when coupled to pivot housing (376) via anvil coupling section (380). Therefore, due to the secure pivotal coupling, the operator may attempt to suitably manipulate stapler (310) in accordance with the description herein without halves (312, 314) inadvertently decoupling at a proximal pivotal coupling.

The operator may then utilize stapler (310) in accordance with the description herein. When the operator desires to decouple halves (312, 314), the operator may pinch, or otherwise actuate latch head (386) into latch aperture (384) such that engagement shoulder no longer engages the portion of pivot housing (376) defining latch aperture (384). Simultaneously, the operator may pull anvil half (314) away from pivot housing (376) until anvil coupling section (380) is entirely removed from hollow interior (390) of pivot housing (376).

While in the current example, pivot pin (374) and side flanges (322) pivotally couple proximal frame portion (318) and pivot housing (376), any other suitable mechanism may be used to pivotally couple pivot housing (376) with proximal frame portion (318) as would be apparent to one skilled in the art in view of the teachings herein, such as a living hinge substantially similar to living hinge (304) described above.

While in the current example, pivot housing (376) associated with the cartridge half (312), this is merely optional, as pivot housing (376) may associate with anvil half (314) and anvil coupling section (380) may associate with cartridge half (312).

C. First Linear Surgical Stapler with Magnetic Separation Mechanism

FIGS. 19-22 show an exemplary linear surgical stapler (410) that may be used in replacement of linear surgical stapler (10) described above. As will be described in greater detail below, linear surgical stapler (410) include a proximal coupling assembly (470) that allows for easy coupling and decoupling of a cartridge half (412) and an anvil half (414) while ensuring a secure proximal pivotal relationship between halves (412, 414).

Linear surgical stapler (410) may be substantially similar to linear surgical stapler (10) described above, with differences elaborated below. Therefore, linear surgical stapler (412) includes cartridge half (412) and anvil half (414), which are substantially similar to cartridge half (12) and anvil half (14), described above, with differences elaborated below.

Cartridge half (412) includes an elongate cartridge channel (416), a proximal frame (418) having upright side flanges (422), a firing assembly (430), and a clamp lever (440) having an elongate arm (444) and a pair of opposed jaws (448); which are substantially similar to elongate cartridge channel (16), proximal frame (18), upright side flanges (22), firing assembly (100), clamp lever (40), elongate arm (44), and opposed jaws (48) described above, respectively, with differences elaborated below.

Anvil half (414) includes an elongate anvil channel (460), a proximal frame portion (not shown), a distal jaw portion (464), a latch pin (468), and a shroud (478); which are substantially similar to elongate anvil channel (60), proximal frame portion (62), distal jaw portion (64), latch pin (68), and shroud (78) described above, respectively, with differences elaborated below. While not shown, it should be understood proximal frame portion (not shown) is housed within shroud (478), similar to proximal frame portion (62) being housed within shroud (78) described above.

While cartridge half (12) and anvil half (14) include tapered notches (26) and proximal pin (70), respectively, in order to provide a temporary pivotal coupling between cartridge half (12) and anvil half (14); linear surgical stapler (410) includes a proximal coupling assembly (470) that allows for temporary coupling between cartridge half (412) and anvil half (414) while also ensuring a secure proximal pivotal relationship between halves (412, 414).

Figure 21:
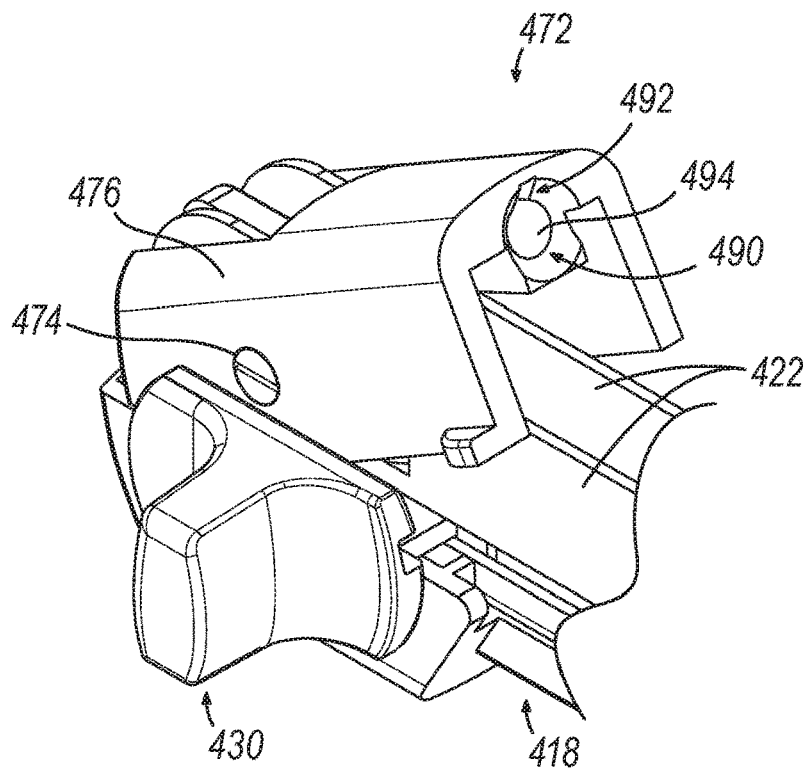
FIG. 21 depicts a perspective view of a proximal portion of the cartridge half of FIG. 19.

Latching proximal coupling assembly (470) includes a pivoting cartridge section (472) and an anvil coupling section (480). As best shown in FIG. 21, pivoting cartridge section (472) includes a pivot pin (474) and a pivot housing (476). Pivot housing (476) is pivotally coupled with a proximal section of proximal frame portion (418) via pivot pin (474) associated with side flanges (422).

Unlike proximal pin (70) described above, pivot pin (474) is configured to remain pivotably coupled with side flanges (422) such that during exemplary use, pivot pin (474) and pivot housing (476) may not disassociate with proximal frame portion (418). In other words, pivot housing (476) is attached to side flanges (422) such that pivot housing (476) may pivot relative to proximal frame (418) about the axis defined by pivot pin (474), but pivot housing (476) may not otherwise detach or disassociate with proximal frame portion (418) during exemplary use. For example, if the operator held cartridge half (412) solely by grasping pivot housing (476), pivot housing (476) and proximal frame portion (418) will remain coupled via interaction between pivot pin (474) and side flanges (422).

Pivot housing (476) defines a magnetic recess (490) and a stability block recess (492). Magnetic recess (490) has a magnetic surface (494). Recesses (490, 492) are dimensioned to selectively house anvil coupling section (480). As will be described in greater detail below, pivot housing (476) is configured to selectively couple with anvil half (414) via anvil coupling section (480) in order to establish a secure pivotably coupling between anvil half (414) and proximal frame portion (418).

Figure 22:
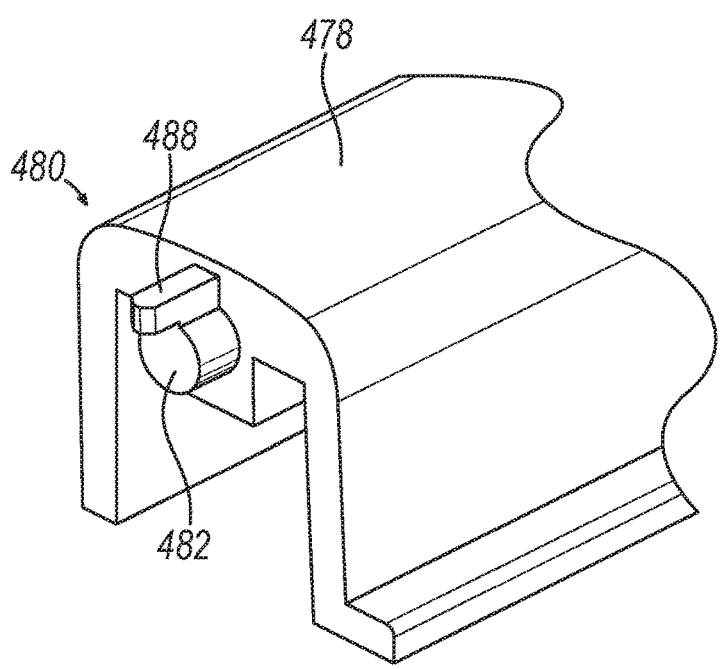
FIG. 22 depicts a perspective view of a proximal portion of the anvil half of FIG. 19.

As best shown in FIG. 22, anvil coupling section (480) includes a stability block (488) and magnetic body (482) both extending proximally from shroud (478). Stability block (488) is dimensioned to fit within the confines of stability block recess (492) of pivoting cartridge section (472) when anvil coupling section (480) is attached to pivoting cartridge section (472) in accordance with the description herein. Stability block (388) fits within recess (492) to sufficiently inhibit lateral or rotational motion of block (388) relative to recess (492).

Similarly, magnetic body (482) is dimensioned to fit within the confines of magnetic recess (490) when anvil coupling section (480) is attached to pivoting cartridge section (472) in accordance with the description herein. Magnetic body (482) and magnetic surface (494) are magnetically attracted to each other with sufficient magnetic force to inhibit distal longitudinal motion of anvil half (414) relative to pivot housing (476) when magnetic body (482) is housed within magnetic recess (490) in accordance with the description herein. Any suitable magnetic relationship between body (482) and surface (494) may be used as would be apparent to one skilled in the art in view of the teachings herein.

Figure 19:
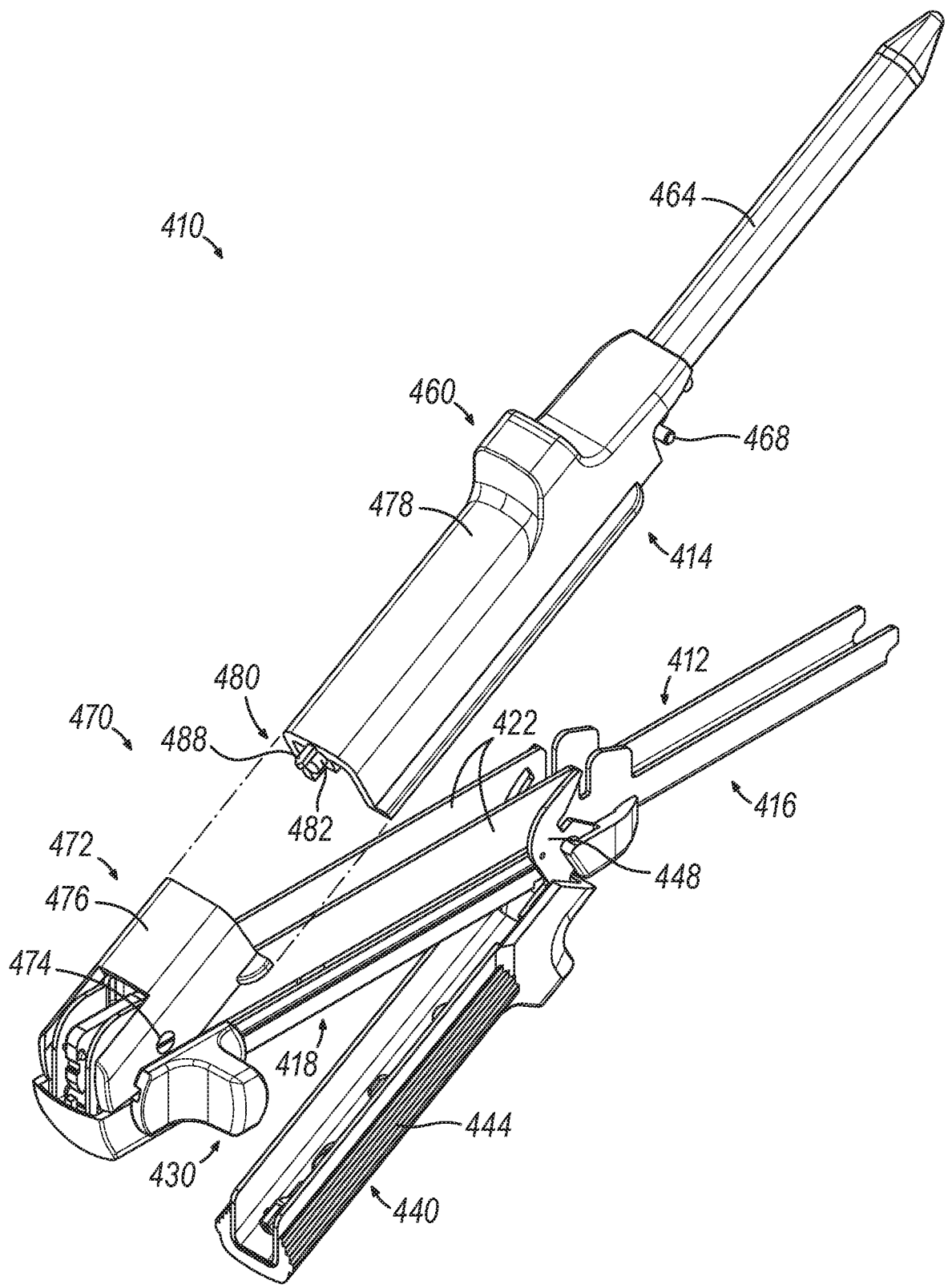
FIG. 19 depicts a perspective view of an alternative linear surgical stapler, showing a cartridge half and an anvil half of the stapler separated from each other with a clamp lever of the cartridge half in an open position.
Figure 20:
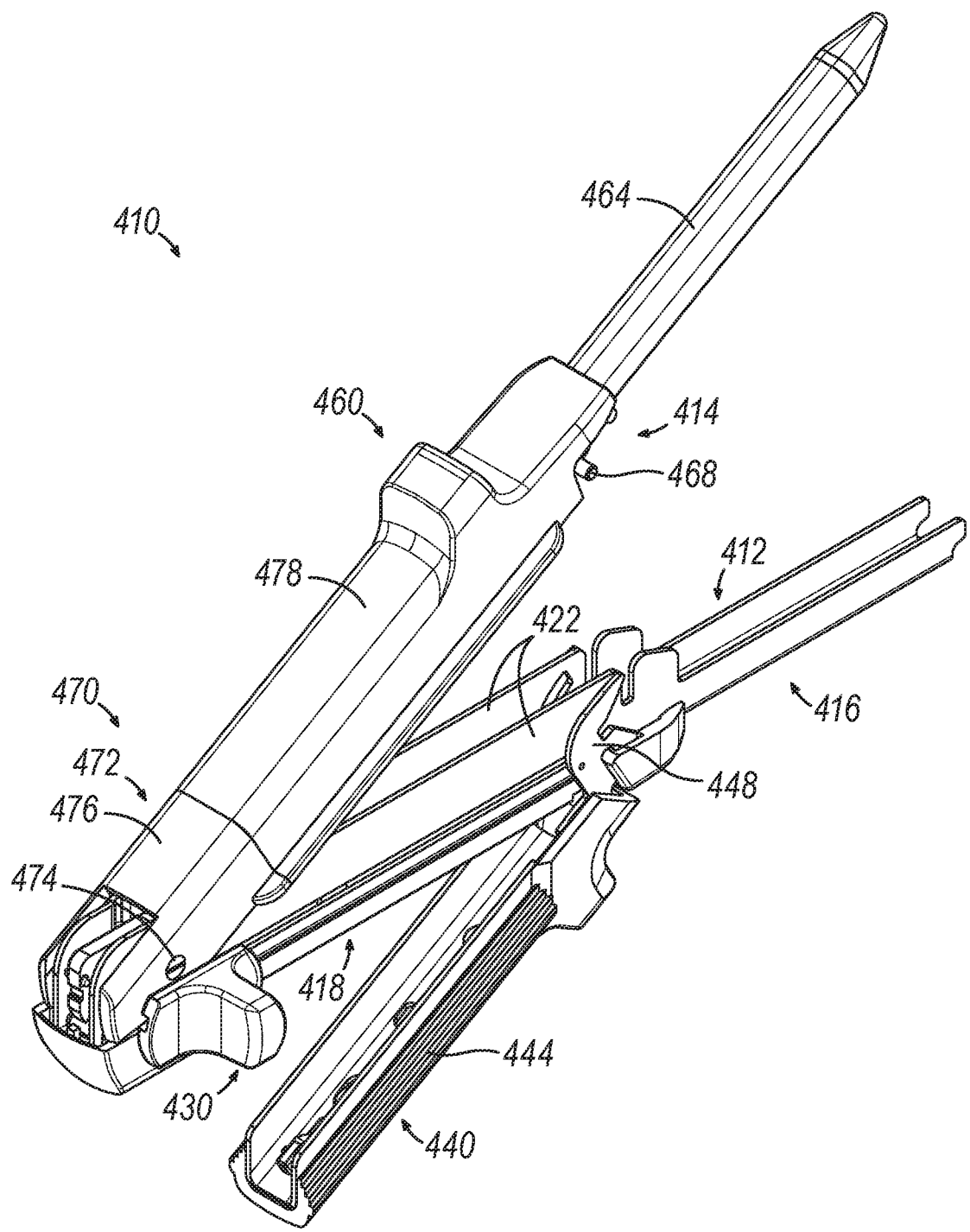
FIG. 20 depicts a perspective view of the linear surgical stapler of FIG. 19, showing the cartridge half and the anvil half of the stapler coupled together with the clamp lever of the cartridge half in the open position.

FIGS. 19-20 show an exemplary assembly of anvil half (414) with cartridge half (412) via proximal coupling assembly (470). First, as shown in FIG. 19, the operator may align the open end of pivot housing (476) with the proximal end of anvil coupling section (480). Next, as shown between FIGS. 19-20, the operator may insert magnetic body (482) and stability block (482) into respective recesses (490, 492) of pivot housing (476).

Once magnetic body (482) is housed within recess (490), magnetic attraction between body (482) and recess (490)

may inhibit distal longitudinal motion of anvil half (414) relative to pivot housing (476). Additionally, engagement between stability block (488) and recess (492) may be sufficient to prevent lateral or rotational motion between anvil half (414) and pivot housing (476). Therefore, once suitably inserted into pivot housing (476), anvil half (414) may be sufficiently attached to pivot housing (476) such that anvil half (414) is also pivotally coupled to proximal frame (418) of cartridge half (412).

Since pivot housing (476) has a secure pivotal coupling with proximal frame portion (418), as described above, anvil half (414) also has a secure pivotal coupling when coupled to pivot housing (476) via anvil coupling section (480). Therefore, due to the secure pivotal coupling, the operator may attempt to suitably manipulate stapler (410) in accordance with the description herein without halves (412, 414) inadvertently decoupling at a proximal pivotal coupling.

The operator may then utilize stapler (410) in accordance with the description herein. When the operator desires to decouple halves (412, 414), the operator may pull anvil half (414) away from pivot housing (476) to overcome the magnetic attraction between body (482) and recess (490) until anvil coupling section (480) is entirely removed from pivoting cartridge section (472).

While in the current example, pivot pin (474) and side flanges (422) pivotally couple proximal frame portion (418) and pivot housing (476), any other suitable mechanism may be used to pivotally couple pivot housing (476) with proximal frame portion (418) as would be apparent to one skilled in the art in view of the teachings herein, such as a living hinge substantially similar to living hinge (304) described above.

While in the current example, pivot housing (476) associated with the cartridge half (412), this is merely optional, as pivot housing (476) may associate with anvil half (414) and anvil coupling section (480) may associate with cartridge half (412).

D. Second Linear Surgical Stapler with Magnetic Separation Mechanism

FIGS. 23-26 show an exemplary linear surgical stapler (510) that may be used in replacement of linear surgical stapler (10) described above. As will be described in greater detail below, linear surgical stapler (510) include a proximal coupling assembly (570) that allows for easy coupling and decoupling of a cartridge half (512) and an anvil half (514) while ensuring a secure proximal pivotal relationship between halves (512, 514).

Linear surgical stapler (510) may be substantially similar to linear surgical stapler (10) described above, with differences elaborated below. Therefore, linear surgical stapler (512) includes cartridge half (512) and anvil half (514), which are substantially similar to cartridge half (12) and anvil half (14), described above, with differences elaborated below.

Cartridge half (512) includes an elongate cartridge channel (516), a proximal frame (518) having upright side flanges (522), and a firing assembly (530); which are substantially similar to elongate cartridge channel (16), proximal frame (18), upright side flanges (22), and firing assembly (100), described above, respectively, with differences elaborated below. While not specifically shown, cartridge half (512) may also have a clamp lever having an elongate arm and a pair of opposed jaws; which may be substantially similar to clamp lever (40), elongate arm (44), and opposed jaws (48) described above Anvil half (514) includes an elongate anvil channel (560), a proximal frame portion (not shown), a distal jaw portion (564), a latch pin (now shown), and a shroud (578); which are substantially similar to elongate anvil channel (60), proximal frame portion (62), distal jaw portion (64), latch pin (68), and shroud (78) described above, respectively, with differences elaborated below. While not shown, it should be understood proximal frame portion (not shown) is housed within shroud (578), similar to proximal frame portion (62) being housed within shroud (78) described above.

While cartridge half (12) and anvil half (14) include tapered notches (26) and proximal pin (70), respectively, in order to provide a temporary pivotal coupling between cartridge half (12) and anvil half (14); linear surgical stapler (510) includes a proximal coupling assembly (570) that allows for temporary coupling between cartridge half (512) and anvil half (514) while also ensuring a secure proximal pivotal relationship between halves (512, 514).

Figure 24:
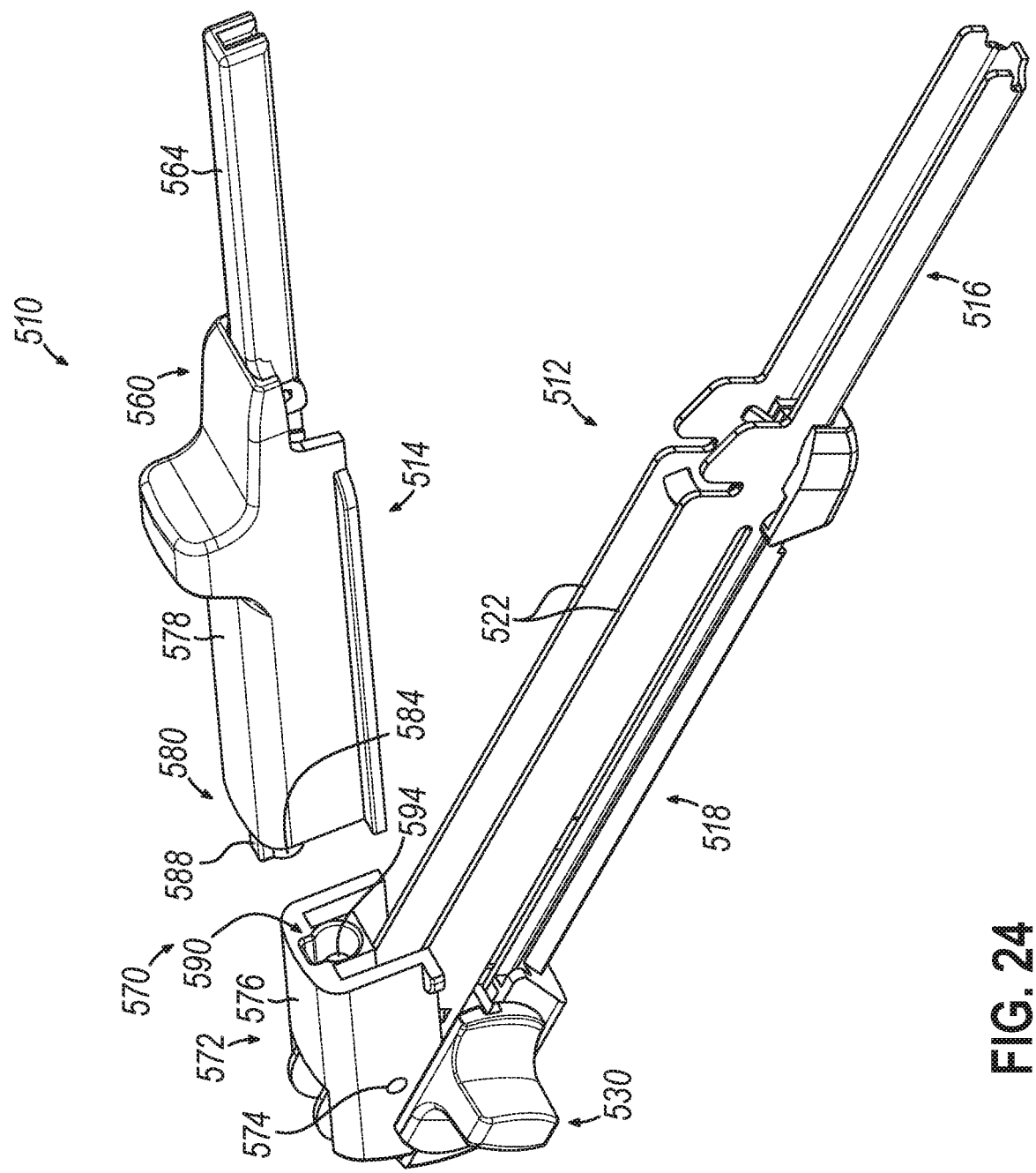
FIG. 24 depicts another perspective view of the linear surgical stapler of FIG. 23, showing the cartridge half and the anvil half of the stapler separated from each other.
Figure 25:
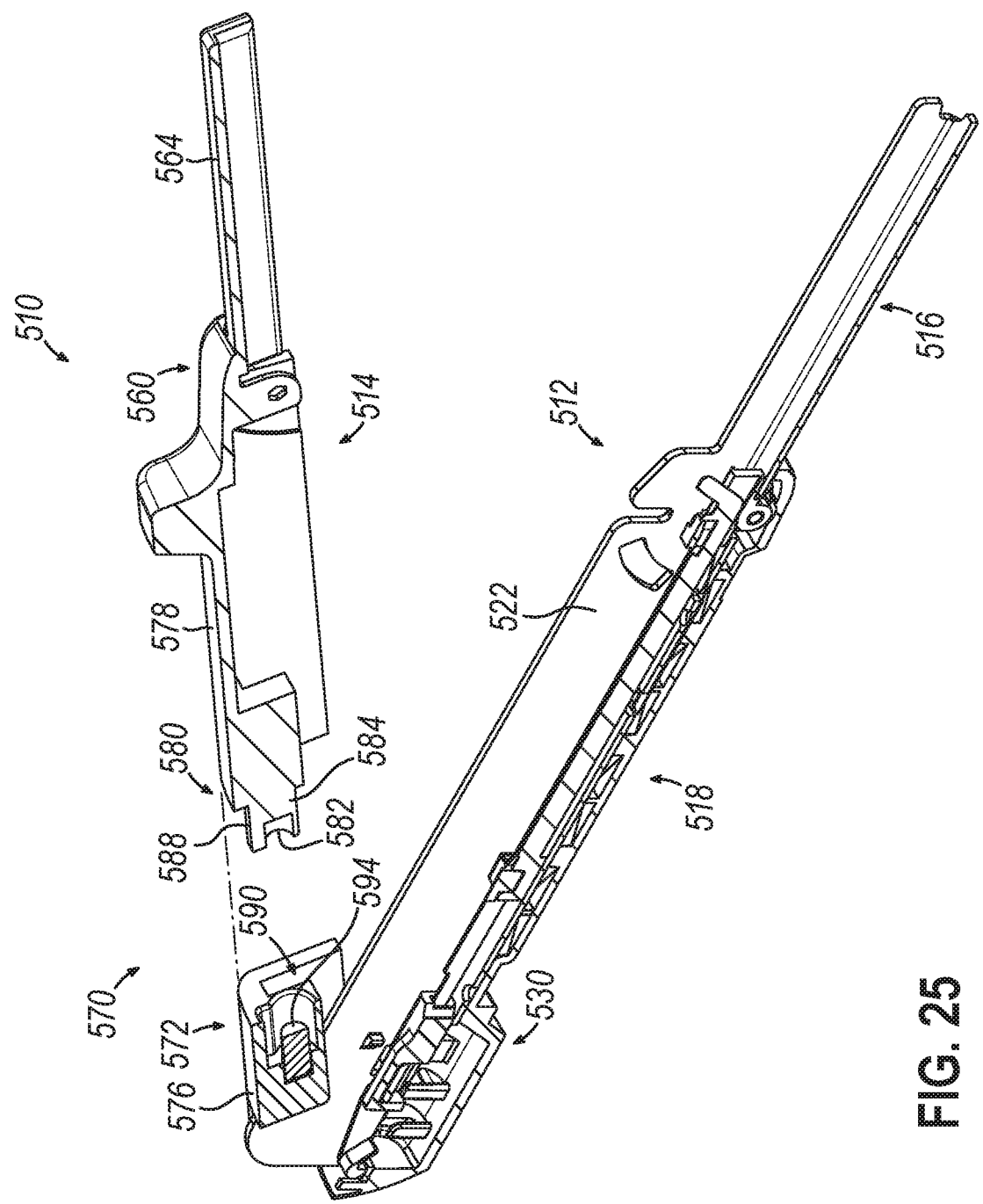
FIG. 25 depicts a cross-sectional view of the linear surgical stapler of FIG. 23, showing the cartridge half and the anvil half of the stapler separated from each other.

Latching proximal coupling assembly (570) includes a pivoting cartridge section (572) and an anvil coupling section (580). As best shown in FIGS. 24-25, pivoting cartridge section (572) includes a pivot pin (574) and a pivot housing (576). Pivot housing (576) is pivotally coupled with a proximal section of proximal frame portion (518) via pivot pin (574) associated with side flanges (522).

Unlike proximal pin (70) described above, pivot pin (574) is configured to remain pivotably coupled with side flanges (522) such that during exemplary use, pivot pin (574) and pivot housing (576) may not disassociate with proximal frame portion (518). In other words, pivot housing (576) is attached to side flanges (522) such that pivot housing (576) may pivot relative to proximal frame (518) about the axis defined by pivot pin (574), but pivot housing (576) may not otherwise detach or disassociate with proximal frame portion (518) during exemplary use. For example, if the operator held cartridge half (512) solely by grasping pivot housing (576), pivot housing (576) and proximal frame portion (518) will remain coupled via interaction between pivot pin (574) and side flanges (522).

Pivot housing (576) defines a keyhole recess (590) that houses a magnetic element (594). Keyhole recess (590) are dimensioned to selectively house anvil coupling section (580). As will be described in greater detail below, pivot housing (576) is configured to selectively couple with anvil half (514) via anvil coupling section (580) in order to establish a secure pivotably coupling between anvil half (514) and proximal frame portion (518).

Figure 23:
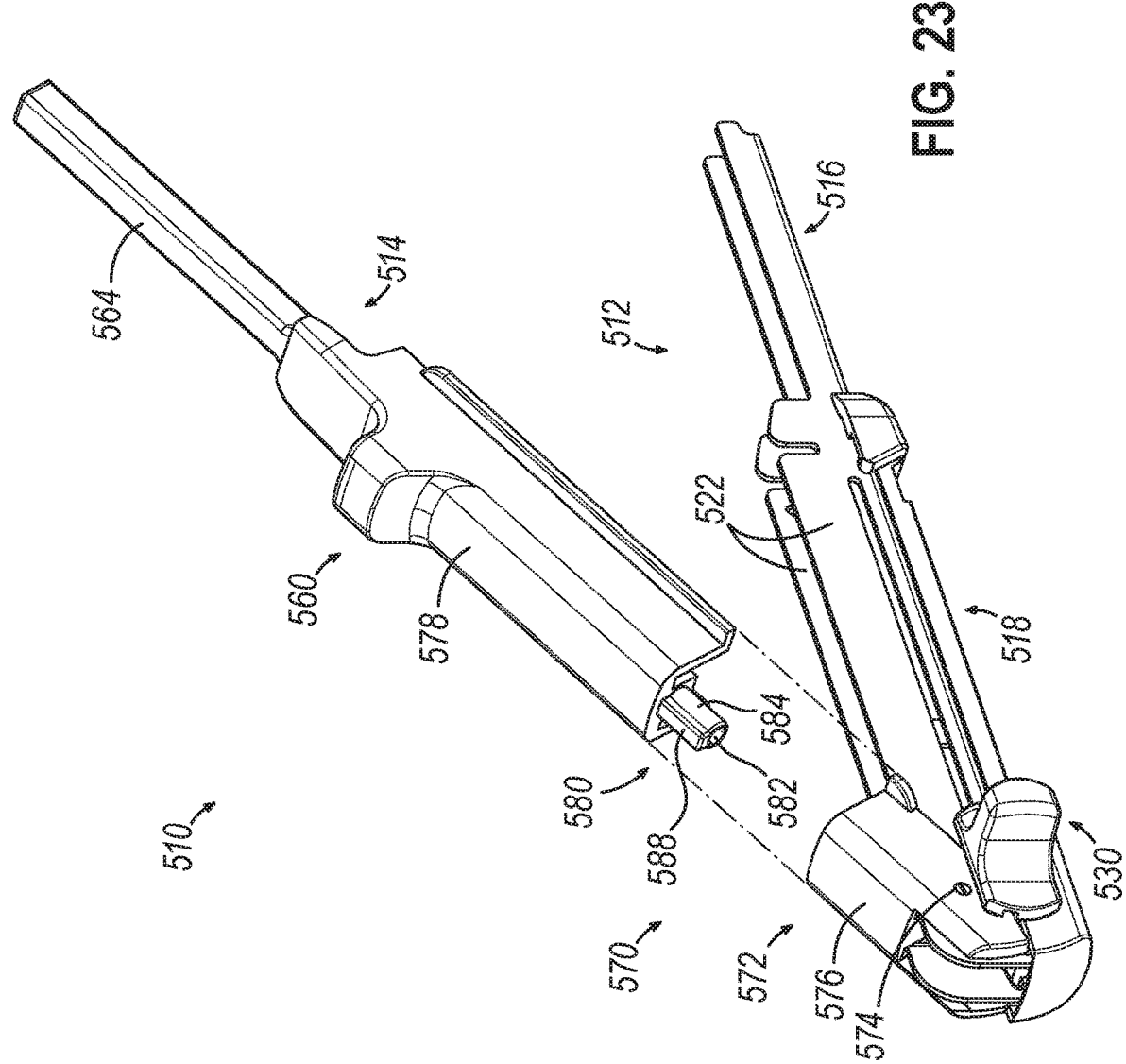
FIG. 23 depicts a perspective view of an alternative linear surgical stapler, showing a cartridge half and an anvil half of the stapler separated from each other.

As best shown in FIGS. 23 and 25, anvil coupling section (580) includes a complementary key-shaped body (588) extending proximally from shroud (578). Key-shaped body (588) has a tubular portion (584) with a magnetic interior surface (582). Key shaped body (588) is dimensioned to fit within the confines of keyhole (590) of pivoting cartridge section (572) when anvil coupling section (580) is attached to pivoting cartridge section (572) in accordance with the description herein. Key-shaped body (588) and keyhole (590) are dimension to sufficiently inhibit lateral or rotational motion of key-shaped body (588) relative to keyhole (590).

Similarly, magnetic element (594) is dimensioned to fit without the interior of tubular portion (584) when anvil coupling section (580) is attached to pivoting cartridge section (572) in accordance with the description herein. Magnetic element (594) and magnetic surface (582) are magnetically attracted to each other with sufficient magnetic force to inhibit distal longitudinal motion of anvil half (514) relative to pivot housing (576) when magnetic body (582) is housed within tubular portion (584) in accordance with the description herein. Any suitable magnetic relationship between body (582) and surface (582) may be used as would be apparent to one skilled in the art in view of the teachings herein.

Figure 26:
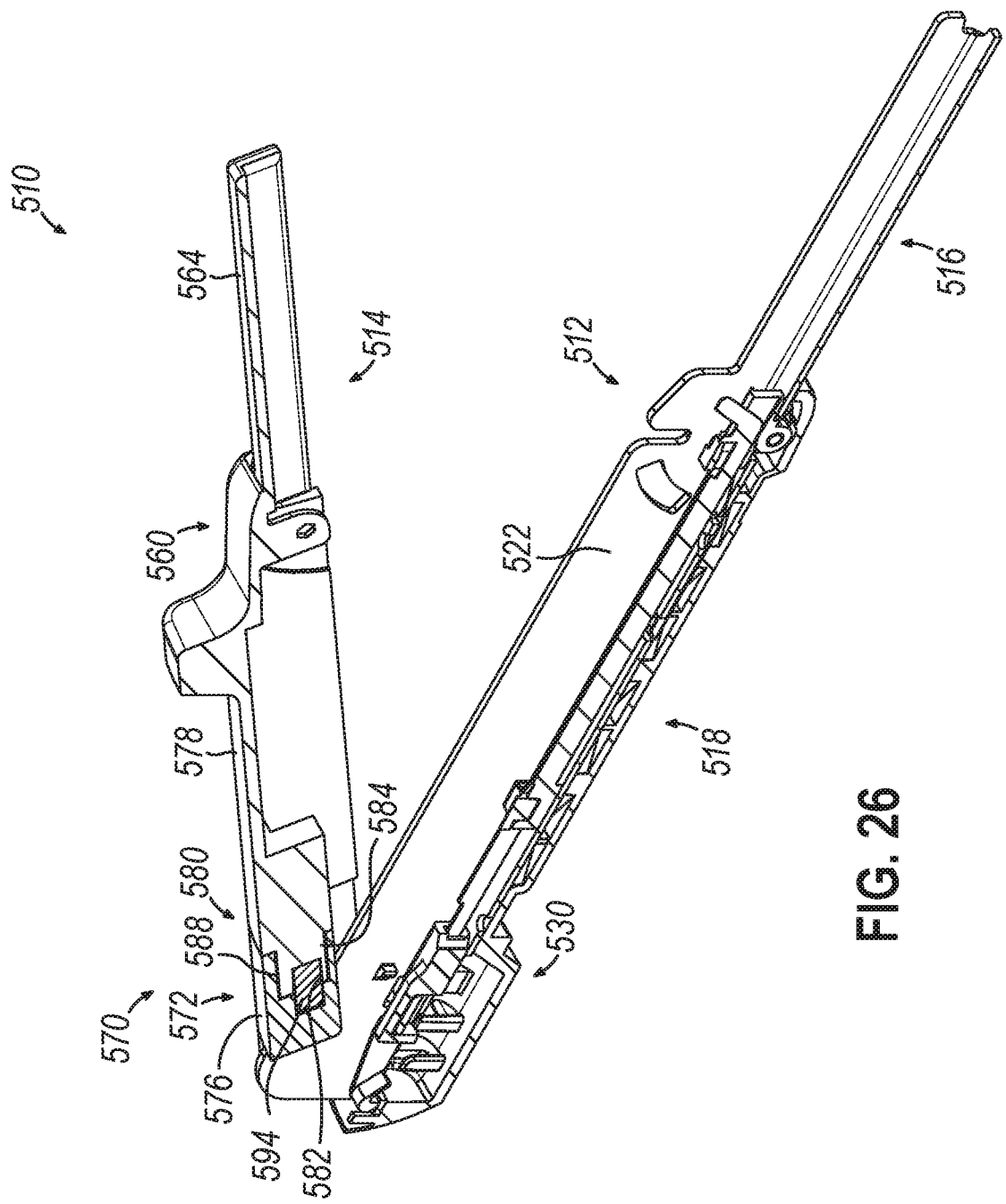
FIG. 26 depicts a cross-sectional view of the linear surgical stapler of FIG. 23, showing the cartridge half and the anvil half of the stapler coupled with each other.

FIGS. 25-26 show an exemplary assembly of anvil half (514) with cartridge half (512) via proximal coupling assembly (570). First, as shown in FIG. 25, the operator may align the open end of pivot housing (576) with the proximal end of anvil coupling section (580). Next, as shown between FIGS. 25-26, the operator may insert key-shaped body (588) into key-hole (590) such that magnetic element (594) is inserted into tubular portion (584)

Once magnetic body (594) is housed within tubular portion (584), magnetic attraction between body (594) and surface (582) may inhibit distal longitudinal motion of anvil half (514) relative to pivot housing (576). Additionally, engagement between key-shaped body (588) and keyhole (590) may be sufficient to prevent lateral or rotational motion between anvil half (514) and pivot housing (576). Therefore, once suitably inserted into pivot housing (576), anvil half (514) may be sufficiently attached to pivot housing (576) such that anvil half (514) is also pivotally coupled to proximal frame (418) of cartridge half (412).

Since pivot housing (576) has a secure pivotal coupling with proximal frame portion (518), as described above, anvil half (514) also has a secure pivotal coupling when coupled to pivot housing (576) via anvil coupling section (580). Therefore, due to the secure pivotal coupling, the operator may attempt to suitably manipulate stapler (510) in accordance with the description herein without halves (512, 514) inadvertently decoupling at a proximal pivotal coupling.

The operator may then utilize stapler (510) in accordance with the description herein. When the operator desires to decouple halves (512, 514), the operator may pull anvil half (514) away from pivot housing (576) to overcome the magnetic attraction between body (594) and surface (582) until anvil coupling section (580) is entirely removed from pivoting cartridge section (572).

While in the current example, pivot pin (574) and side flanges (452) pivotally couple proximal frame portion (518) and pivot housing (576), any other suitable mechanism may be used to pivotally couple pivot housing (576) with proximal frame portion (518) as would be apparent to one skilled in the art in view of the teachings herein, such as a living hinge substantially similar to living hinge (304) described above.

While in the current example, pivot housing (576) associated with the cartridge half (512), this is merely optional, as pivot housing (576) may associate with anvil half (514) and anvil coupling section (580) may associate with cartridge half (512).

E. Linear Surgical Stapler with Frictional Separation Mechanism

FIGS. 27-30 show an exemplary linear surgical stapler (610) that may be used in replacement of linear surgical stapler (10) described above. As will be described in greater detail below, linear surgical stapler (610) include a proximal coupling assembly (670) that allows for easy coupling and decoupling of a cartridge half (612) and an anvil half (614) while ensuring a secure proximal pivotal relationship between halves (612, 614).

Linear surgical stapler (610) may be substantially similar to linear surgical stapler (10) described above, with differences elaborated below. Therefore, linear surgical stapler (612) includes cartridge half (612) and anvil half (614), which are substantially similar to cartridge half (12) and anvil half (14), described above, with differences elaborated below.

Cartridge half (612) includes an elongate cartridge channel (616), a proximal frame (618) having upright side flanges (622), and a firing assembly (630); which are substantially similar to elongate cartridge channel (16), proximal frame (18), upright side flanges (22), and firing assembly (100) described above, respectively, with differences elaborated below. While not particularly shown, it should be understood cartridge half (612) may also include a clamp lever (not shown) having an elongate arm (not shown) and a pair of opposed jaws (not shown); which may be substantially similar to clamp lever (40), elongate arm (44), and opposed jaws (48) described above, respectively.

Anvil half (614) includes an elongate anvil channel (660), a proximal frame portion (not shown), a distal jaw portion (664), a latch pin (not shown), and a shroud (678); which are substantially similar to elongate anvil channel (60), proximal frame portion (62), distal jaw portion (64), latch pin (68), and shroud (78) described above, respectively, with differences elaborated below. While not shown, it should be understood proximal frame portion (not shown) is housed within shroud (678), similar to proximal frame portion (62) being housed within shroud (78) described above.

While cartridge half (12) and anvil half (14) include tapered notches (26) and proximal pin (70), respectively, in order to provide a temporary pivotal coupling between cartridge half (12) and anvil half (14); linear surgical stapler (610) includes a proximal coupling assembly (670) that allows for temporary coupling between cartridge half (612) and anvil half (614) while also ensuring a secure proximal pivotal relationship between halves (612, 614).

Figure 30:
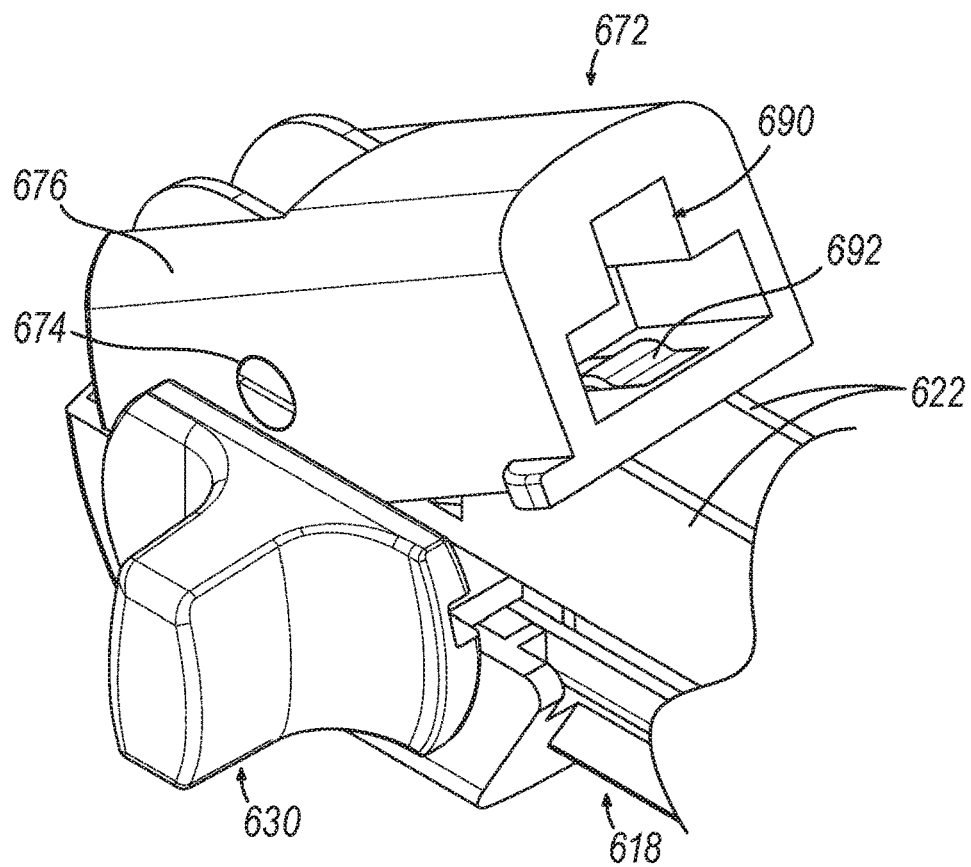
FIG. 30 depicts a perspective view of the proximal end of the cartridge half of FIG. 27.

Latching proximal coupling assembly (670) includes a pivoting cartridge section (672) and an anvil coupling section (680). As best shown in FIG. 30, pivoting cartridge section (672) includes a pivot pin (674) and a pivot housing (676). Pivot housing (676) is pivotally coupled with a proximal section of proximal frame portion (618) via pivot pin (674) associated with side flanges (622).

Unlike proximal pin (70) described above, pivot pin (674) is configured to remain pivotably coupled with side flanges (622) such that during exemplary use, pivot pin (674) and pivot housing (676) may not disassociate with proximal frame portion (618). In other words, pivot housing (676) is attached to side flanges (622) such that pivot housing (676) may pivot relative to proximal frame (618) about the axis defined by pivot pin (674), but pivot housing (676) may not otherwise detach or disassociate with proximal frame portion (618) during exemplary use. For example, if the operator held cartridge half (612) solely by grasping pivot housing (676), pivot housing (676) and proximal frame portion (618) will remain coupled via interaction between pivot pin (674) and side flanges (622).

Pivot housing (676) defines a complementary hollow interior (690) housing a leaf spring (692). Hollow interior (690) is dimensioned to selectively house anvil coupling section (680). As will be described in greater detail below, pivot housing (676) is configured to selectively couple with anvil half (614) via anvil coupling section (680) in order to establish a secure pivotably coupling between anvil half (614) and proximal frame portion (618).

Figure 27:
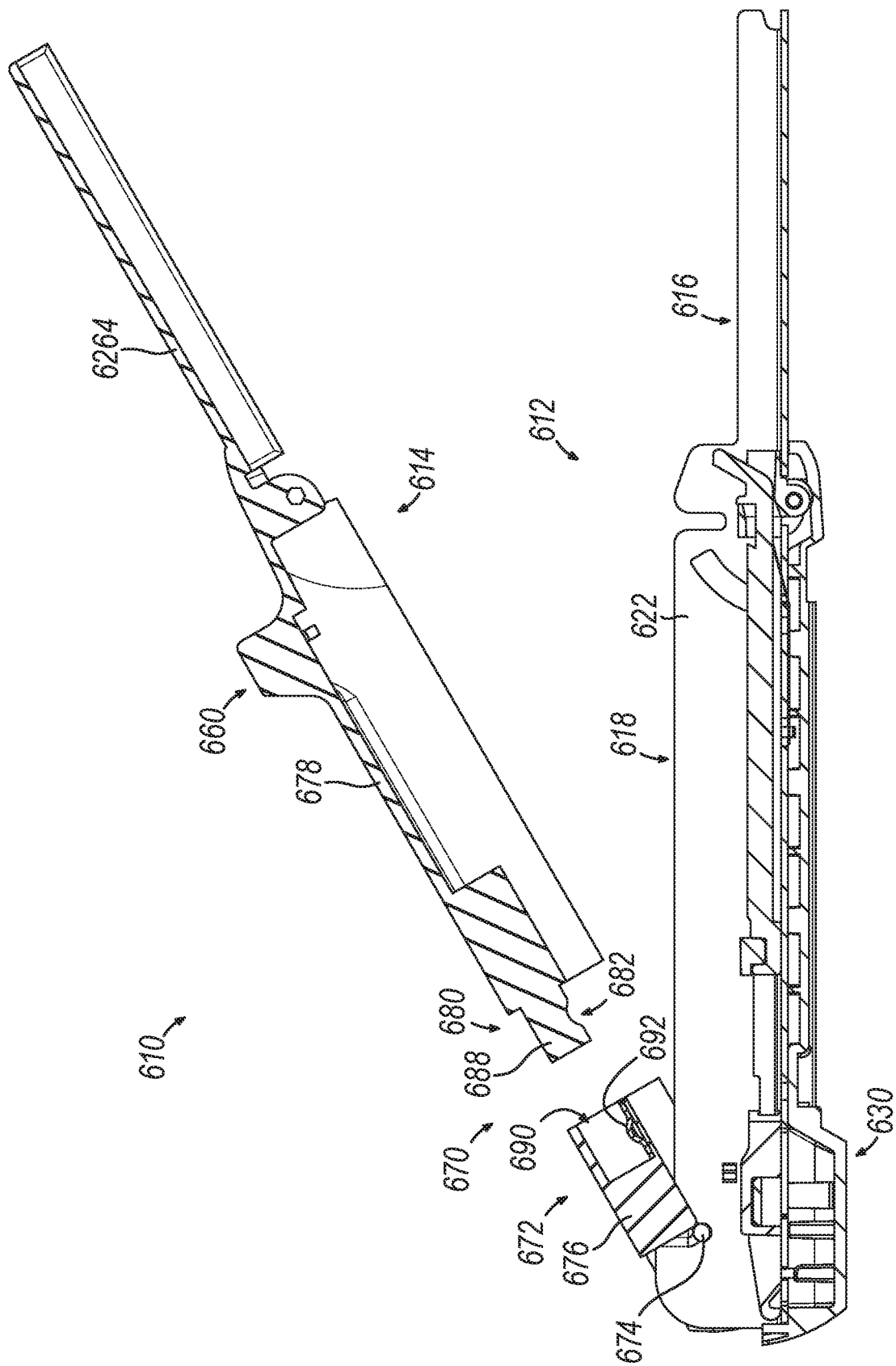
FIG. 27 depicts a cross-sectional view of an alternative linear surgical stapler, showing a cartridge half and an anvil half of the stapler separated from each other
Figure 29:
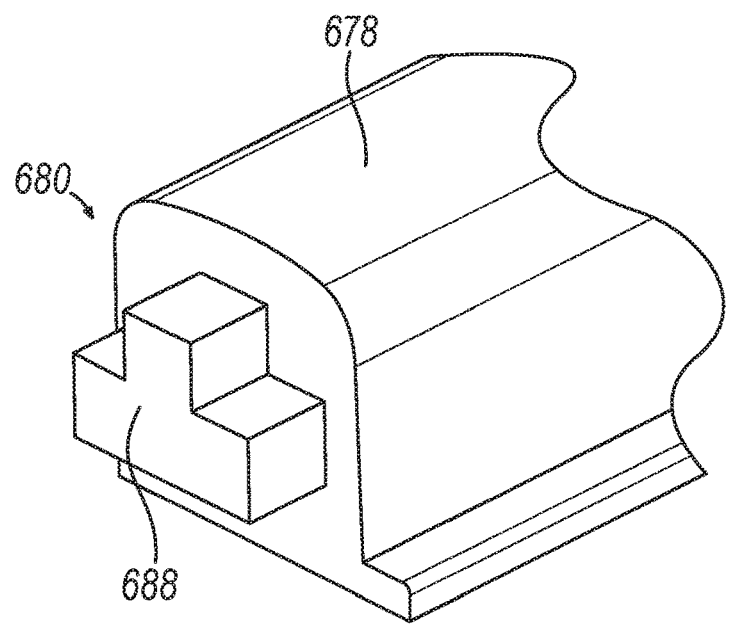
FIG. 29 depicts a perspective view of the proximal end of the anvil half of FIG. 27.

As best shown in FIGS. 27 and 29, anvil coupling section (680) includes a stability block (688) extending proximally from shroud (678). The underside of stability block (688) defines a recess (682) dimensioned to interact with leaf spring (692) of pivot housing (676). Stability block (688) is dimensioned to fit within the confines of complementary hollow interior (690) of pivoting cartridge section (672) when anvil coupling section (680) is attached to pivoting cartridge section (672) in accordance with the description herein.

Leaf spring (692) is dimensioned to fit within recess (692) when anvil coupling section (680) is attached to pivoting cartridge section (672). Leaf spring (692) is sufficiently resilient to flex in response to a sufficient force to accommodate coupling of anvil coupling section (680) with pivoting cartridge section (672) in accordance with the description herein. Additionally, leaf spring (692) is sufficiently resilient to suitably inhibit distal longitudinal motion of anvil half (614) relative to pivot housing (676) when leaf spring (692) is housed within recess (682) in accordance with the description herein.

Figure 28:
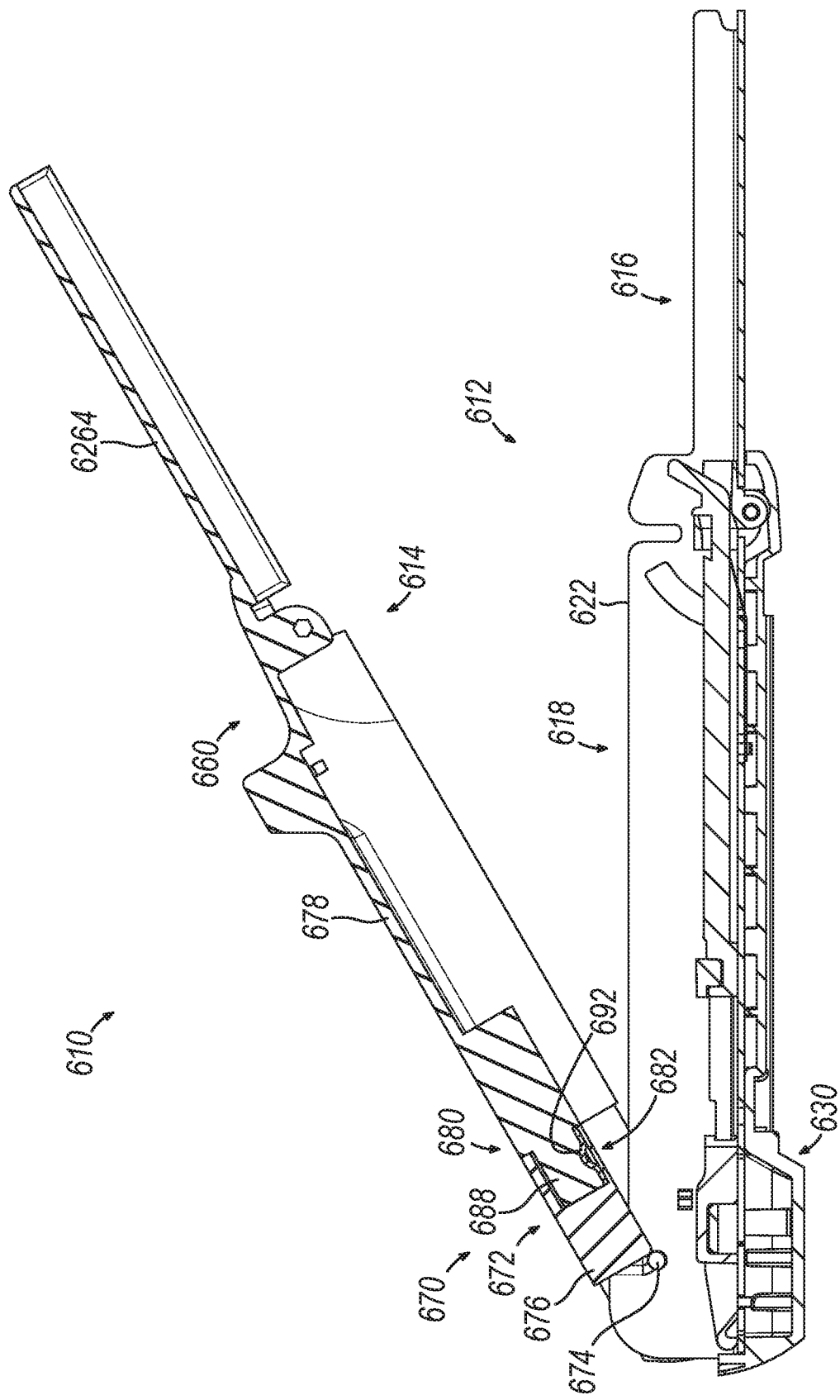
FIG. 28 depicts a cross-sectional view of the linear surgical stapler of FIG. 27, showing the cartridge half and the anvil half of the stapler coupled with each other.

FIGS. 27-28 show an exemplary assembly of anvil half (614) with cartridge half (612) via proximal coupling assembly (670). First, as shown in FIG. 27, the operator may align the open end of pivot housing (676) with the proximal end of anvil coupling section (680). Next, as shown between FIGS. 27-28, the operator may insert anvil coupling section (680) into complementary opening (690) of pivot housing (676) with sufficient force to bend leaf spring (692). When leaf spring (692) is within recess (682), leaf spring (692) may return to a relaxed position and/or engage the surface defining recess (682) to provide a frictional braking force. At the moment shown in FIG. 28, anvil coupling section (280) is fully inserted within hollow interior (290).

Once leaf spring (692) is housed within recess (682), the frictional braking force between leaf spring (692) and recess (682) may inhibit distal longitudinal motion of anvil half (614) relative to pivot housing (676). Additionally, engagement between stability block (688) and complementary opening (690) may be sufficient to prevent lateral or rotational motion between anvil half (614) and pivot housing (676). Therefore, once suitably inserted into pivot housing (676), anvil half (614) may be sufficiently attached to pivot housing (676) such that anvil half (614) is also pivotally coupled to proximal frame (618) of cartridge half (612).

Since pivot housing (676) has a secure pivotal coupling with proximal frame portion (618), as described above, anvil half (614) also has a secure pivotal coupling when coupled to pivot housing (676) via anvil coupling section (680). Therefore, due to the secure pivotal coupling, the operator may attempt to suitably manipulate stapler (610) in accordance with the description herein without halves (612, 614) inadvertently decoupling at a proximal pivotal coupling.

The operator may then utilize stapler (610) in accordance with the description herein. When the operator desires to decouple halves (612, 614), the operator may pull anvil half (614) away from pivot housing (676) with sufficient force for overcome the frictional braking force between leaf spring (692) is within recess (682) in order to deform leaf spring (692) until anvil coupling section (680) is entirely removed from hollow interior (690) of pivot housing (676).

While in the current example, pivot pin (674) and side flanges (622) pivotally couple proximal frame portion (618) and pivot housing (676), any other suitable mechanism may be used to pivotally couple pivot housing (676) with proximal frame portion (618) as would be apparent to one skilled in the art in view of the teachings herein, such as a living hinge substantially similar to living hinge (304) described above.

While in the current example, pivot housing (676) associated with the cartridge half (612), this is merely optional, as pivot housing (676) may associate with anvil half (614) and anvil coupling section (680) may associate with cartridge half (612).

While in the current example, a leaf spring (692) is used to provide the frictional braking force to inhibit distal longitudinal motion of anvil half (614) relative to pivot housing (676), any other suitable alternative mechanisms may be used as would be apparent to one skilled in the art in view of the teachings herein. For instance, a compression spring, a resilient plastic detent, an elastomeric body, etc. may be used in order to provide a sufficient frictional braking force in accordance with the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, the apparatus comprising: (a) a first portion comprising: (i) a first handle, and (ii) a first jaw extending distally from the first handle; (b) a second portion configured to selectively couple with the first portion, wherein the second portion is configured to pivot about a proximal location relative to the first portion while coupled with the first portion, the second portion comprising: (i) a second handle, and (ii) a second jaw extending distally from the second handle; (c) a latching member movably coupled with either the first portion or the second portion, wherein the latching member is configured to drive the first jaw and the second jaw toward a fully closed configuration for clamping tissue between the first jaw and the second jaw, wherein the first jaw and the second jaw are operable to cooperate to cut and staple the tissue in the fully closed configuration; and (d) a proximal coupling assembly configured to selectively attach the first portion with the second portion such that the second portion is pivotally coupled with the first portion, wherein the proximal coupling assembly comprises: (i) a pivot body pivotally attached to the first portion at the proximal location, and (ii) a coupling body associated with the second portion, wherein the coupling body is configured to engage the pivot body at a location distal to the proximal location to selectively attach the first portion with the second portion.

Example 2

The apparatus of Example 1, wherein the latching member is pivotally coupled with the first portion about a distal pivot location.

Example 3

The apparatus of any one or more of Examples 1 through 2, wherein the first jaw comprises a cartridge receiving channel configured to selectively couple with a staple cartridge.

Example 4

The apparatus of any one or more of Examples 1 through 3, wherein the second jaw comprises an anvil.

Example 5

The apparatus of any one or more of Examples 1 through 4, further comprising a firing assembly associated with the first handle, wherein the firing assembly comprises a knife member.

Example 6

The apparatus of Example 5, wherein the firing assembly is configured to drive a plurality of staples from a staple cartridge associate with the first jaw.

Example 7

The apparatus of any one or more of Examples 1 through 6, wherein the pivot body is pivotally coupled with the first portion via a pivot pin.

Example 8

The apparatus of any one or more of Examples 1 through 7, wherein the pivot body is pivotally coupled with the first portion via a living hinge.

Example 9

The apparatus of any one or more of Examples 1 through 8, wherein the pivot body defines a hollow interior and a latch aperture.

Example 10

The apparatus of Example 9, wherein the coupling body comprises a resilient latch configured to selectively coupled with the pivot body via the latch aperture.

Example 11

The apparatus of Example 10, wherein the coupling body further comprises a stability body, wherein the pivot body defines a distally open slot, wherein the stability body is dimensioned to fit within the distally open slot.

Example 12

The apparatus of any one or more of Examples 1 through 11, wherein the coupling body and the pivot body are configured to engage the pivot body via a magnetic attraction.

Example 13

The apparatus of Example 12, wherein the coupling body defines a keyhole recess and the pivot body comprises key-shaped body configured to fit within the keyhole recess.

Example 14

The apparatus of Example 12, wherein the pivot body defines a keyhole recess and the coupling body comprises a key-shaped body configured to fit within the keyhole recess.

Example 15

The apparatus of any one or more of Examples 1 through 14, wherein the pivot body and the coupling body are configured to engage each other via a resilient member.

Example 16

An apparatus, the apparatus comprising: (a) an end effector, wherein the end effector comprises: (i) a first jaw, and (ii) a second jaw configured to pivot about a proximal pivot relative to the first jaw between an open configuration, a partially closed configuration, and a fully closed configuration in order to grasp tissue, wherein the first jaw and the second jaw are operable to cooperate to cut and staple tissue in the fully closed configuration; (b) handle assembly, wherein the handle assembly comprises: (i) a first arm extending proximally from the first jaw, (ii) a second arm extending proximally from the second jaw along a longitudinal axis, and (iii) a latching member movably coupled with the first arm at a distal pivot location, wherein the latching member is configured to engage the second arm or the second jaw to drive the second jaw from the partially closed configuration toward the fully closed configuration; and (c) a proximal coupling assembly configured to selectively couple the first arm with the second arm, wherein the proximal coupling assembly comprises: (i) a housing pivotally attached to the first arm at the proximal pivot, and (ii) an attachment member associated with the second arm, wherein the attachment member is configured to align with the housing along the longitudinal axis in order to selectively couple with the housing to pivotally couple the second jaw with the first jaw about the proximal pivot.

Example 17

The apparatus of Example 16, wherein the attachment member comprises a resilient latch.

Example 18

The apparatus of any one or more of Examples 16 through 17, wherein the attachment member comprises a magnetic body.

Example 19

The apparatus of any one or more of Examples 16 through 18, wherein the housing defines a hollow interior dimensioned to receive at least a portion of the attachment member.

Example 20

An apparatus, the apparatus comprising: (a) a first portion comprising: (i) a first handle, and (ii) a first jaw extending distally from the first handle; (b) a second portion comprising: (i) a second handle, (ii) a second jaw extending distally from the second handle, and (iii) a latching projection, wherein the second portion is configured to pivotally couple with the first portion at a proximal location in an open configuration; (c) a latching lever pivotally coupled with the first portion, wherein the latching lever is configured to pivot the first jaw and the second jaw from a partially closed configuration toward a fully closed configuration for clamping tissue between the first jaw and the second jaw, wherein the first jaw and the second jaw are operable to cooperate to cut and staple the tissue in the fully closed configuration; and (d) a proximal coupling assembly configured to selectively couple the first portion with the second portion at location distal to the proximal coupling, wherein the proximal coupling assembly comprises a housing pivotally attached to the first handle at the proximal location, wherein the housing is configured to selectively attach to the second handle.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. Pub. No. 2019/0239883, entitled "Releasable Coupling Features for Proximal Portions of Linear Surgical Stapler," published on Aug. 8, 2019, issued as U.S. Pat. No. 10,898,197 on Jan. 26, 2021; U.S. Pub. No. 2020/0046351, entitled "Decoupling Mechanism for Linear Surgical Stapler," published on Feb. 13, 2020, issued as U.S. Pat. No. 11,033,266 on Jun. 15, 2021; U.S. Pub. No. 2020/0046353, entitled "Clamping Assembly for Linear Surgical Stapler," published on Feb. 13, 2020; U.S. application Ser. No. 16/886,919, entitled "Surgical Linear Cutter Wishbone Separation Mechanism with Detent," filed on even date herewith, issued as U.S. Pat. No. 11,224,425 on Jan. 18, 2022; and U.S. application Ser. No. 16/886,920, entitled "Pin Trap Mechanism for Surgical Linear Cutter," filed on even date herewith, issued as U.S. Pat. No. 11,219,454 on Jan. 11, 2022. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. An apparatus, the apparatus comprising:
(a) a first portion comprising:
(i) a first handle, and
(ii) a first jaw extending distally from the first handle;
(b) a second portion configured to selectively couple with the first portion, wherein the second portion is configured to pivot about a proximal location relative to the first portion while coupled with the first portion, the second portion comprising:

(i) a second handle, and
(ii) a second jaw extending distally from the second handle;
(c) a latching member movably coupled with either the first portion or the second portion, wherein the latching member is configured to drive the first jaw and the second jaw toward a fully closed configuration for clamping tissue between the first jaw and the second jaw, wherein the first jaw and the second jaw are operable to cooperate to cut and staple the tissue in the fully closed configuration; and
(d) a proximal coupling assembly configured to selectively attach the first portion with the second portion such that the second portion is pivotally coupled with the first portion, wherein the proximal coupling assembly comprises:
(i) a pivot body pivotally attached to the first portion at the proximal location, and
(ii) a coupling body associated with the second portion, wherein the coupling body is configured to engage the pivot body at a location distal to the proximal location to selectively attach the first portion with the second portion.

2. The apparatus of claim 1, wherein the latching member is pivotally coupled with the first portion about a distal pivot location.

3. The apparatus of claim 1, wherein the first jaw comprises a cartridge receiving channel configured to selectively couple with a staple cartridge.

4. The apparatus of claim 1, wherein the second jaw comprises an anvil.

5. The apparatus of claim 1, further comprising a firing assembly associated with the first handle, wherein the firing assembly comprises a knife member.

6. The apparatus of claim 5, wherein the firing assembly is configured to drive a plurality of staples from a staple cartridge associate with the first jaw.

7. The apparatus of claim 1, wherein the pivot body is pivotally coupled with the first portion via a pivot pin.

8. The apparatus of claim 1, wherein the pivot body is pivotally coupled with the first portion via a living hinge.

9. The apparatus of claim 1, wherein the pivot body defines a hollow interior and a latch aperture.

10. The apparatus of claim 9, wherein the coupling body comprises a resilient latch configured to be selectively coupled with the pivot body via the latch aperture.

11. The apparatus of claim 10, wherein the coupling body further comprises a stability body, wherein the pivot body defines a distally open slot, wherein the stability body is dimensioned to fit within the distally open slot.

12. The apparatus of claim 1, wherein the coupling body and the pivot body are configured to engage the pivot body via a magnetic attraction.

13. The apparatus of claim 12, wherein the coupling body defines a keyhole recess and the pivot body comprises key-shaped body configured to fit within the keyhole recess.

14. The apparatus of claim 12, wherein the pivot body defines a keyhole recess and the coupling body comprises a key-shaped body configured to fit within the keyhole recess.

15. The apparatus of claim 1, wherein the pivot body and the coupling body are configured to engage each other via a resilient member.

16. An apparatus, the apparatus comprising:
(a) an end effector, wherein the end effector comprises:
(i) a first jaw, and
(ii) a second jaw configured to pivot about a proximal pivot relative to the first jaw between an open configuration, a partially closed configuration, and a fully closed configuration in order to grasp tissue, wherein the first jaw and the second jaw are operable to cooperate to cut and staple tissue in the fully closed configuration;
(b) a handle assembly, wherein the handle assembly comprises:
(i) a first arm extending proximally from the first jaw,
(ii) a second arm extending proximally from the second jaw along a longitudinal axis, and
(iii) a latching member movably coupled with the first arm, wherein the latching member is configured to engage the second arm or the second jaw to drive the second jaw from the partially closed configuration toward the fully closed configuration; and
(c) a proximal coupling assembly configured to selectively couple the first arm with the second arm, wherein the proximal coupling assembly comprises:
(i) a housing pivotally attached to the first arm at the proximal pivot, and
(ii) an attachment member associated with the second arm, wherein the attachment member is configured to align with the housing along the longitudinal axis in order to selectively couple with the housing to pivotally couple the second jaw with the first jaw about the proximal pivot.

17. The apparatus of claim 16, wherein the attachment member comprises a resilient latch.

18. The apparatus of claim 16, wherein the attachment member comprises a magnetic body.

19. The apparatus of claim 16, wherein the housing defines a hollow interior dimensioned to receive at least a portion of the attachment member.

20. An apparatus, the apparatus comprising:
(a) a first portion comprising:
(i) a first handle, and
(ii) a first jaw extending distally from the first handle;
(b) a second portion comprising:
(i) a second handle,
(ii) a second jaw extending distally from the second handle, and
(iii) a latching projection, wherein the second portion is configured to pivotally couple with the first portion at a proximal location in an open configuration;
(c) a latching lever pivotally coupled with the first portion, wherein the latching lever is configured to pivot the first jaw and the second jaw from a partially closed configuration toward a fully closed configuration for clamping tissue between the first jaw and the second jaw, wherein the first jaw and the second jaw are operable to cooperate to cut and staple the tissue in the fully closed configuration; and
(d) a proximal coupling assembly configured to selectively couple the first portion with the second portion at location distal to the proximal coupling, wherein the proximal coupling assembly comprises a housing pivotally attached to the first handle at the proximal location, wherein the housing is configured to selectively attach to the second handle.

* * * * *